(12) United States Patent
Van Tilborg

(10) Patent No.: US 10,426,741 B2
(45) Date of Patent: Oct. 1, 2019

(54) COLLAGEN AND ELASTIN STIMULATING COMPOUND AND TOPICAL COMPOSITIONS COMPRISING SUCH COMPOUND

(71) Applicant: Joventis S.A., Strassen (LU)

(72) Inventor: Reiner Van Tilborg, Strassen (LU)

(73) Assignee: Joventis, S.A., Strassen (LU)

( * ) Notice: Subject to any disclaimer, the term of this patent is extended or adjusted under 35 U.S.C. 154(b) by 0 days.

(21) Appl. No.: 14/917,941

(22) PCT Filed: Sep. 11, 2014

(86) PCT No.: PCT/EP2014/069424
§ 371 (c)(1),
(2) Date: Mar. 9, 2016

(87) PCT Pub. No.: WO2015/036498
PCT Pub. Date: Mar. 19, 2015

(65) Prior Publication Data
US 2016/0213623 A1 Jul. 28, 2016

(30) Foreign Application Priority Data

Sep. 11, 2013 (LU) .......................................... 92277

(51) Int. Cl.
*A61K 31/015* (2006.01)
*A61K 9/00* (2006.01)
(Continued)

(52) U.S. Cl.
CPC .............. *A61K 31/015* (2013.01); *A61K 8/31* (2013.01); *A61K 9/0014* (2013.01); *A61K 9/06* (2013.01);
(Continued)

(58) Field of Classification Search
CPC ...... A61K 31/015; A61K 8/31; A61K 9/0014; A61K 9/06; A61K 47/12; A61K 47/44; A61Q 19/08; C07C 13/39; C07C 2602/42
See application file for complete search history.

(56) References Cited

U.S. PATENT DOCUMENTS

2016/0262995 A1* 9/2016 Van Tilborg ............. A61K 8/31

FOREIGN PATENT DOCUMENTS

DE 285092 A5 12/1990

OTHER PUBLICATIONS

Clinical trial: retrieved from internet: http://joventis.com/en/index.html under "Clinical Trial". Retrieved on Nov. 23, 2016.*
(Continued)

*Primary Examiner* — Hong Yu
(74) *Attorney, Agent, or Firm* — Umberg Zipser LLP

(57) ABSTRACT

The present invention relates to a bicyclic compound of Formula (I) and to a composition for a cosmetic and therapeutic use and to a composition comprising an acceptable vehicle and an effective amount of the compound of Formula (I):

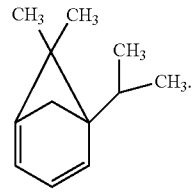

Formula (I)

9 Claims, 14 Drawing Sheets

(51) Int. Cl.
  *A61Q 7/00*  (2006.01)
  *A61K 8/31*  (2006.01)
  *A61K 47/44*  (2017.01)
  *A61Q 3/00*  (2006.01)
  *A61K 9/06*  (2006.01)
  *A61K 47/12*  (2006.01)
  *A61K 8/36*  (2006.01)
  *A61Q 19/08*  (2006.01)
  *A61Q 19/02*  (2006.01)
  *A61Q 19/00*  (2006.01)
  *C07C 13/39*  (2006.01)
  *A61K 8/92*  (2006.01)

(52) U.S. Cl.
  CPC ............. *A61K 47/12* (2013.01); *A61K 47/44* (2013.01); *A61Q 19/08* (2013.01); *C07C 13/39* (2013.01); *C07C 2602/42* (2017.05)

(56) References Cited

OTHER PUBLICATIONS

Conference: retrieved from internet: http://joventis.com/en/index.html under "Conferences". Retrieved on Nov. 23, 2016.*

Gert Kobrichl, Bredt Compounds and the Bredt Rule, Tetrahedron Angew. Chern. internat. Edit. Chern. Ber. Chern. Ber. Bull. Chern. SOC. Iap. J. Org. Chem. F. A. Neugebauer, Chern. Ber, Jan. 1, 1970 (Jan. 1, 1970), pp. 71-2744, XP055115933.

Wilhelm F. Maier et al: "Evaluation and prediction of the stability of bridgehead olefins", Journal of the American Chemical Society, val. 103, No. 8, Apr. 1, 1981 (Apr. 1, 1981 ), pp. 1891-1900, XP055120199, ISSN: 0002-7863.

Ermer et al: "Structures, energies, and reactivities of bridgehead olefins", Zeitschrift Fuer Naturforschung. Teil B, Anorganische Chemie, Organische Chemie, Verlag Der Zeitschrift Fuer Naturforschung, Tuebingen, DE, val. 32B, No. 7, Jan. 1, 1977 (Jan. 1, 1977), pp. 837-839.

Derek L. Ransley: "The Alkylation of Benzene with 1,2-Dichloroalkanes", The Journal of Organic Chemistry vol. 31, No. 11, Nov. 1, 1966 (Nov. 1, 1966), pp. 3595-3599, XP055115841, ISSN: 0022-3263.

Shinji Masuda et al: "The participation effect of halogen atoms in stereospecific Friedei?Crafts alkylations", Journal of the Chemical Society, Chemical Communications, No. 3, Jan. 1, 1980 (Jan. 1, 1980), p. 86, XP055115837, ISSN: 0022-4936.

Kenneth J. Shea et al: "Influence of strain on chemical reactivity. Relative reactivity of torsionally distorted double bonds in MCPBA epoxidations", Journal of the American Chemical Society, vol. 114, No. 8, Apr. 1, 1992 (Apr. 1, 1992 ), pp. 3044-3051, XP055155602, ISSN: 0002-7863.

* cited by examiner

Taxol

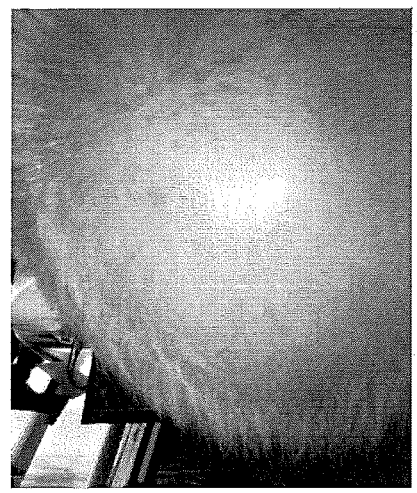
FIG.16
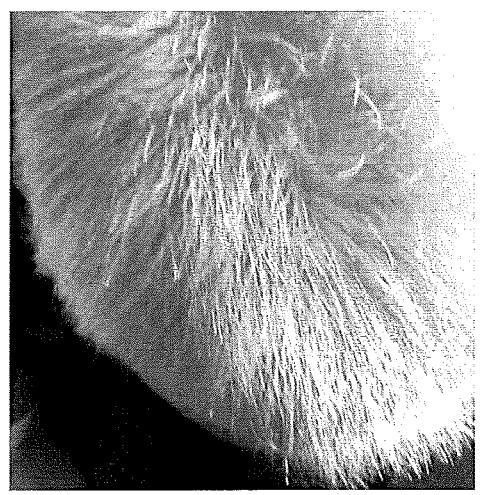
FIG.17
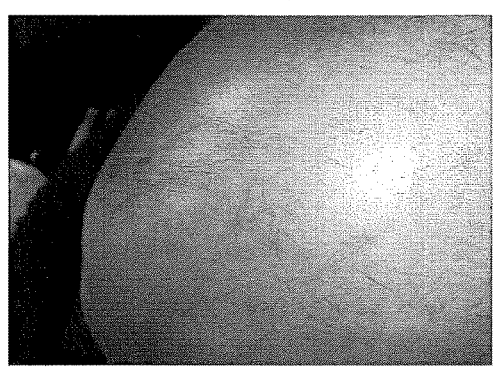　　　　
FIG.18　　　　FIG.19

COLLAGEN AND ELASTIN STIMULATING COMPOUND AND TOPICAL COMPOSITIONS COMPRISING SUCH COMPOUND

The present invention relates to a cosmetic and therapeutic composition comprising an acceptable vehicle and a dermatologically effective amount of a bicyclic compound having the Formula (I):

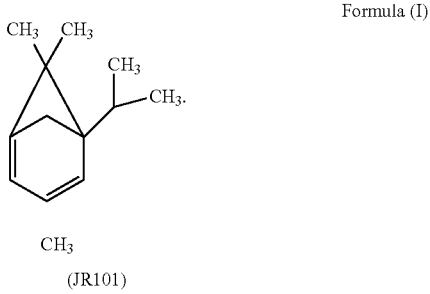

Formula (I)

(JR101)

The present invention also relates to a chemical compound according to Formula (1), a pharmaceutical compound for use according, a topical composition having the compound of Formula (1), the use of the composition for lifting up the levels of collagen and elastin in the skin, the use of the composition for hair and/or nail growth and skin rejuvenation and skin and/or nail repair, and a cream.

PRIOR ART REFERENCES ARE AS FOLLOWS

Gert Kobrichl (document D1) relates to Bredt compounds and the Bredt rule, tetrahedron Angew. Chem. Internat. Edit. Chem. Ber. Chem. Ber. Bull. Chem. SOC. Lap. J. Org. Chem. F. A. Neugebauer, Chem. Ber, Jan. 1, 1970, pages 71-2744.

Wilhelm F. Maier et al (document D2) concerns the evaluation and prediction of the stability of bridgehead olefins, Journal of the American Chemical Society, vol. 103, no 8, Apr. 1, 1981, pages 1891-1900.

Ermer et al (document D3) discloses structures, energies and reactivities of bridgehead olefins, Zeitschrift für Naturforschung, Teil B, Anorganische chemie, Organische chemie, Tuebingen, vol. 32B, no 7, Jan. 1, 1977, pages 837-839.

Derek L. Ransley (document D4) relates to the alkylation of benzene with 1,2-dichloroalkanes, the journal of organic chemistry, vol. 31, no 11, Nov. 1, 1966, pages 3595-3599.

Shinji Masuda et al (document D5) describes the participation effect of halogen atoms in stereospecific Friedel-Crafts alkylation, journal of the chemical society, chemical communications, no 3, Jan. 1, 1980, pages 86.

DD 285092 (document D6) concerns a process for enhancing the selection of the Friedel-Crafts alkylation of aromates with 1,2-dihalogenalkanes.

Collagen is a protein that gives our skin its structure and gives skin its appearance of smoothness and youth. It is composed of three protein chains wound together in a tight triple helix and works like netting that holds skin cells together. Collagen is continually produced in the body, but as we get older that production begins to slow down. As production slows and the collagen net begins to break down, the skin is one of the first areas we notice it in, with wrinkles and other signs of aging. Collagen makes up approximately 75 percent of our skin. Therefore, the smooth appearance of young, healthy skin is due in large part to the presence of healthy collagen levels. Because of this, beauty seekers around the globe search for new ways to boost collagen levels and repair past collagen damage, some go so far as to inject collagen proteins into the skin to plump wrinkles and add volume to the lips. However, many attempts to stimulate collagen have failed or have only minor effects. Also, putting animal collagen into cosmetic creams can lead to unhealthy side effects (e.g., Curcio & Parish, 2009).

Elastin is another protein found in the skin and tissue of the body. It helps to keep skin flexible but tight, providing a bounce-back reaction if skin is pulled. Enough elastin in the skin means that the skin will return to its normal shape after a pull. It also helps keeping skin smooth as it stretches to accommodate normal activities like flexing a muscle or opening and closing the mouth to talk or eat. As people age, elastin usually depletes, resulting in wrinkled or stretched out skin. Elastin is also used as an ingredient in "anti-aging" skin care products. These proteins however are not from human sources; they typically are harvested from either cows or birds and in theory should promote better skin elasticity. However, these skin products have been shown to have little effect on skin elasticity. It may form a coating on the skin that helps the skin better hold in moisture, but it will not provide more flexibility. In skin care products, this protein does not penetrate the skin layer, which would be needed in order to make the skin more elastic.

Therefore, protecting or stimulating in vivo skin collagen and/or elastin would lead to protect or restore the skin appearance, its flexibility and youth and could prevent or treat hair loss. WO 2001087292 discloses the use of ovotransferrin to preserve collagen and elastin, while WO 2013028266 discloses the use of *Justicia ventricosa, Archidendron clypearia, Abrus fruticulosus* extracts for stimulating the production of collagen and elastin, and WO1997018223A1 the use of bicyclic compounds.

Bicyclic compounds are well known compounds comprising two ring which may be linked either across a bond between two atoms (for example, decalin having a C—C bond shared between two cyclohexane rings) or across a sequence of atoms (bridgehead) or at a single atom (spirocyclic, forming a spiro compound).

"Bredt compounds" are well known bicyclic compounds in the camphene and pinane series wherein the branching points of the carbon bridges (A and B in FIG. 1), known as the bridgeheads, cannot be involved in a carbon double bound. This empirical rule is known as the "Bredt's rule", as discussed in Ulf Peters in "Thesis: Studies Towards Anti-Bredt Ring Systems of Natural Products, the University of Tennessee, Knoxville, August 2002", by Gert Köbrich in "Bredt Compounds and the Bredt Rule", *Angew. Chem. Internat.* Edit Vol 12 (1973) No 6, and by F. A. Neugebauer, in *Chem. Ber*, Jan. 1, 1970, pages 71-2744.

The "Bredt's rule" is generally used to justify the failure to implement certain types of chemical reactions that would have otherwise led to the formation of bicyclic systems with bridgehead π bonds. For example, Bredt's rule explains the failure of some anhydride formations and hydrohalide eliminations (see compounds of FIGS. 2 and 3).

However the Bredt's rule seems not to be valid for homologs of the compound shown in FIG. 4 as bicyclic cycloalkenes could be obtained, either with a double bond placed away from the bridgehead position (Bredt-alkenes) or with a double bond at the bridgehead (anti-Bredt alkenes) as disclosed by Lease, T. G., et al in "A study of the effects of Strain on the Structure and Reactivity of Bridgehead Olefins" *J Am Chem Soc* 1993, and further as natural anti-bredt ring systems occur in natural products, such as taxol (FIG. 1), the synthesis from which was accomplished by Prelog and coworkers in 1940, and which was isolated as a [5.3.1] bicyclic compound type (FIG. 7) with an olefin at the bridgehead position.

Another well-known rule is the "Fawcett Rule" (see F. S Fawcett, *Chem Rev*, 47, 219 (1950)) which states that, for bicyclo[x.y.z]alkenes, "S" (the sum of the numbers of bridge atoms $S=x+y+z$, being for example equal to 9 for the compound represented in FIG. 2, $x=5$, $y=3$, $z=1$) should be no smaller than nine, explaining thus the unsuccessful generation of structure B of the compound of FIG. 8 in favor of structure A). However, as disclosed by J. R Wiseman, J Amer. Chem. Soc 89, 5966 (1967) and *J Amer Chem Soc* 92, 956 (1970) a bicyclo[3.3.1]non-1-ene (FIG. 9), a structure where $S=7$, could have been synthesized.

The apparent inconsistency with Fawcett's rule was explained by Wiseman et al. by comparing the strain in a bicyclic ring with the strain of a trans-cycloalkene. In FIG. 3, for example, the double bond is exocyclic to ring ab but endocyclic to rings ac and bc. In other words the double bond could be viewed as Trans in ring ac and Cis in ring bc (FIG. 10). Based on these findings, Wiseman postulated that a double bond at the bridgehead forms so that it is Trans in the larger of the two rings in which it is endocyclic. All isolable bridgehead olefins are contained in a trans cycloalkenes unit with at least eight carbon atoms. When the trans alkene-containing ring is seven or six membered, bridgehead olefins are predicted not to be observable at room temperature. Unfortunately, this Trans olefin rule does not distinguish among isomeric compounds. To date Wiseman's postulate is the accepted reference for predicting where the double bond in a bicyclic system will form.

The Bredt compounds are presented as being unstable compounds. For example Gert Köbrich presents bridgehead compounds having the sum of the numbers of bridge atoms S being less than 7 as being unstable but this conclusion came up as these compounds are not able, as intermediates, to react in particular chemical reactions.

However, the bridgehead compounds stability can be predicted by calculating the olefin strain (OS) energy, as disclosed by Wilhelm F. Maier et al in *Journal of the American Chemical Society*, vol. 103, no 8, Apr. 1, 1981, pages 1891-1900, and the reactivities of bridgehead compounds can be evaluated, as disclosed by Ermer et al in "Structures, energies and reactivities of bridgehead olefins", *Zeitschrift für Naturforschung, Teil B, Anorganische chemie, Organische chemie, Tuebingen*, vol. 32B, no 7, Jan. 1, 1977, pages 837-839.

Thus, getting stable bridgehead compounds might be an issue emphasizing the need to use the right in chemical reaction conditions, especially for aromatic-based bicyclic compound, knowing some products obtained by reaction of benzene with 1,2-dichloroalkanes (Derek L. Ransley in the *Journal of organic chemistry*, vol. 31, no 11, Nov. 1, 1966, pages 3595-3599), the participation effect of halogen atoms in stereospecific Friedel-Crafts alkylations (Shinji Masuda et al in *Journal of the chemical society, chemical communications*, no 3, Jan. 1, 1980, pages 86) and the selection enhancement in Friedel-Crafts alkylation of aromatic compounds with 1,2-dihalogenalkanes (DD 285 092).

Concerning the mode of preparation of the compound, it is clear from documents D4, D5 and D6 that when reacting 1.2-dichloropropane with toluene under those reaction conditions, the compound obtained by such reaction is different from the compound of the present invention, i.e. from compound of formula (I), as no bridge is formed but the dialkylated product is formed.

SUMMARY OF THE INVENTION

The chemical compound of the present invention is defined in Formula (1).

The present invention provides a solution that does not present the drawbacks of the prior art.

The present invention provides a solution for preventing or treating skin against heat and/or chemical burns or scalds and/or alopecia.

The present invention provides an alternative compound for use as cosmetic or as therapeutic agent for preventing or treating skin against heat and/or chemical burns or scalds and/or alopecia.

The present invention provides a new bicyclic compound as active compound, and a composition comprising such active ingredient, for protecting or stimulating collagen and elastin in human or animal skin.

The cosmetic active compound of formula I of the present invention (JR101) is unique in this way that it stimulates people's own collagen and elastin levels on a natural basis. Moreover, it is designed to repair collagen levels in old skin, up to 100% of its original, youthful value, in a short amount of time. Using this cosmetic formula, the applicant fabricated a cosmetic cream designed to get elastin and collagen levels of facial skin up to 100% of its original value staring from 6 to 10 weeks for 50-70 year old people.

The technical effect of the present invention is to provide a new topical composition for increasing the levels of collagen and elastin in the skin. The effect of the compound of formula (I) is to lift up the levels of collagen and elastin in the skin. The visual effect of the compound of formula (I) is also to increase hair growth, rejuvenate the skin and repair the skin, particularly skin heat and chemical burns or skin scalds. As skin and hair are interrelated, the increase of collagen and elastin in the scalp has also proven to increase hair growth.

No pertinent prior art has been found which use the compound of formula (I) in a cosmetic composition.

The application of the composition of the present invention is to be considered as a cosmetic but also as a therapeutic treatment of the human body which involves a therapeutic aspect due to the prophylactic effect which is indissolubly linked to the cosmetic use.

The problem to be solved by the present invention may be regarded as the provision of an alternative room temperature stable compound for use as a cosmetic or as a therapeutic (medicament) in a topical composition.

The solution to the problem is to use the compound of formula (I) which is stable at room temperature and which does not present the drawbacks of the prior art.

The prior art does not suggest to use at least five sequences of incubation, one sequence being a change of temperature from 4° C. to −80° C. with incubation of 30 minutes and from −80° C. to 40° C. with incubation of 30 minutes and from 40° C. to −80° C. again with incubation of 30 minutes.

The present invention will be better understood with the accompanying figures.

Figure 12:
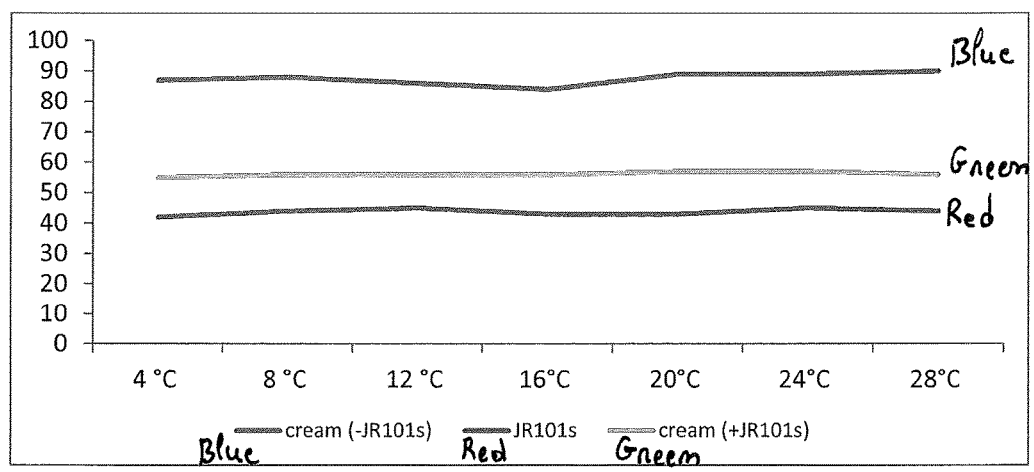

FIG. 12 is a diagram of stability of JR101s incorporated or not in a topical composition. The red curve shows the JR101s HPGC profile at 4, 8, 12, 16, 20, 24 and 28° C. The Green curve show the cream (with JR101s) HPGC profile at 4, 8, 12, 16, 20, 24 and 28° C. The Blue curve show the cream (without JR101s) HPGC profile at 4, 8, 12, 16, 20, 24 and 28° C.

Figure 13:
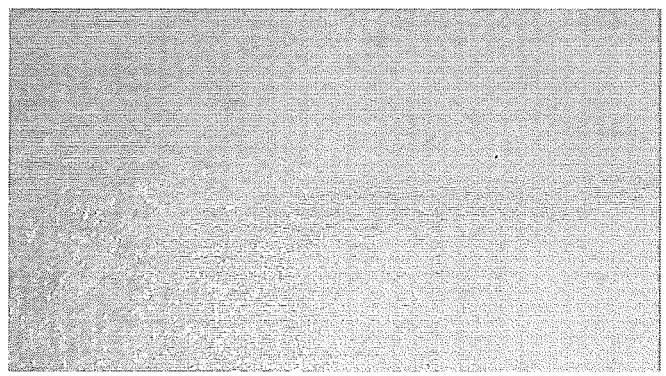

FIG. 13 shows alopecia at day 0 (close up top of head—female subject who lost all body hair after trauma).

Figure 14:

FIG. 14 represents alopecia after 4 months of the same subject as at FIG. 13 after treatment with the compound of formula (I) of the present invention (hair growth is demonstrated).

Figure 15:
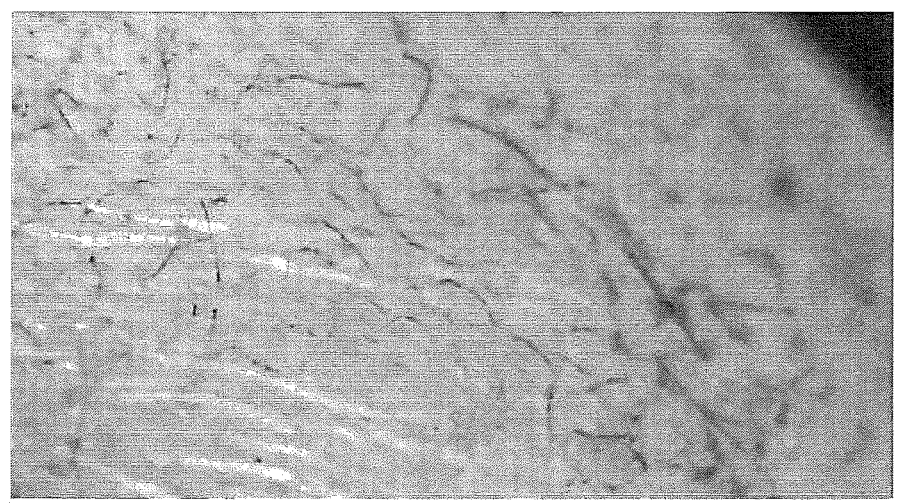

FIG. 15 represents alopecia after 4 months (manually colored new hair) of the same subject as at FIG. 13 after treatment with the compound of formula (I) of the present invention (hair growth is demonstrated).

FIG. 16 represents a balding male at day 0 (complete bald spot and very thing grey hair).

FIG. 17 represents the same subject as at FIG. 16 after 6 months of treatment with the compound of formula (I) of the present invention (hair growth is demonstrated).

FIG. 18 represents a balding male at day 0

Figure 20:
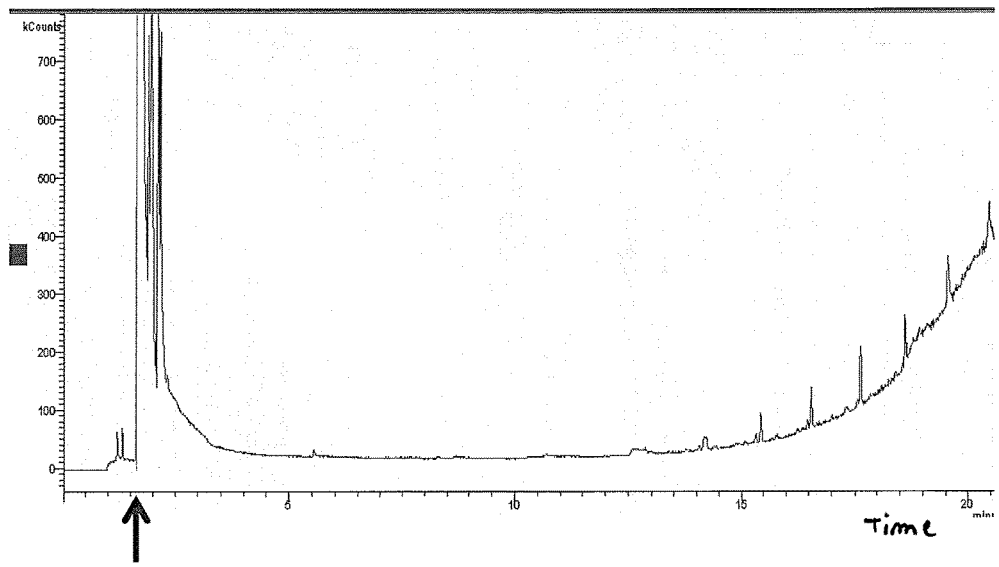

FIG. 19 represents the same subject as at FIG. 18 after 6 months of treatment with the compound of formula (I) of the present invention FIG. 20 shows a representation of the chromatogram of toluene. The Black arrow corresponds to the exit of toluene from the column. Other peaks after that of toluene correspond to contaminants.

Figure 21:
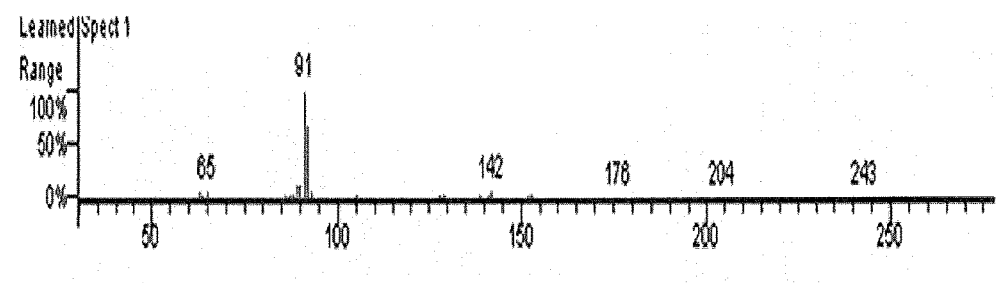

FIG. 21 shows a representation of the mass spectrum of toluene.

Figure 22:
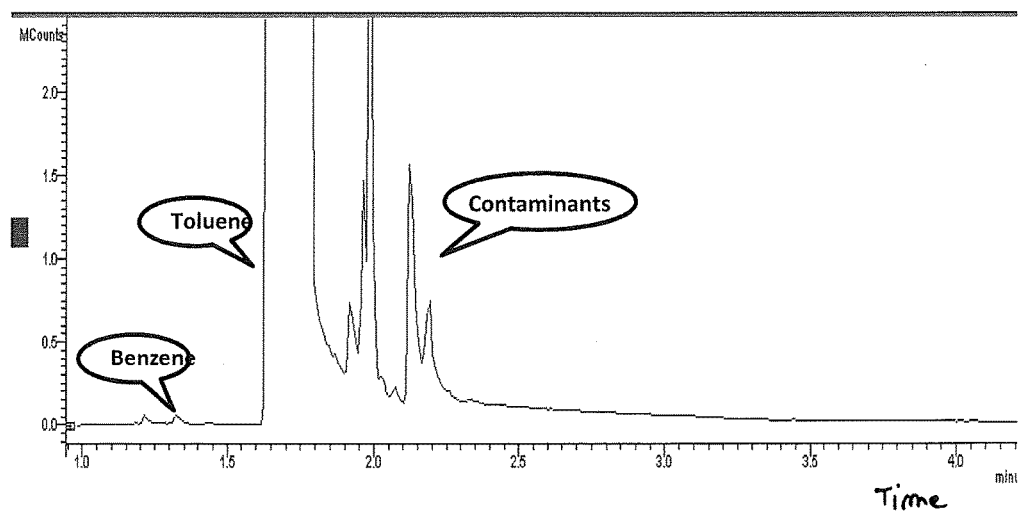

FIG. 22 shows a representation of the chromatogram of toluene and benzene. This experience confirms the percentage of purity of toluene used in JR101s production. We detected benzene and other contaminants (quantity of contaminants is less than 1%).

Figure 23:
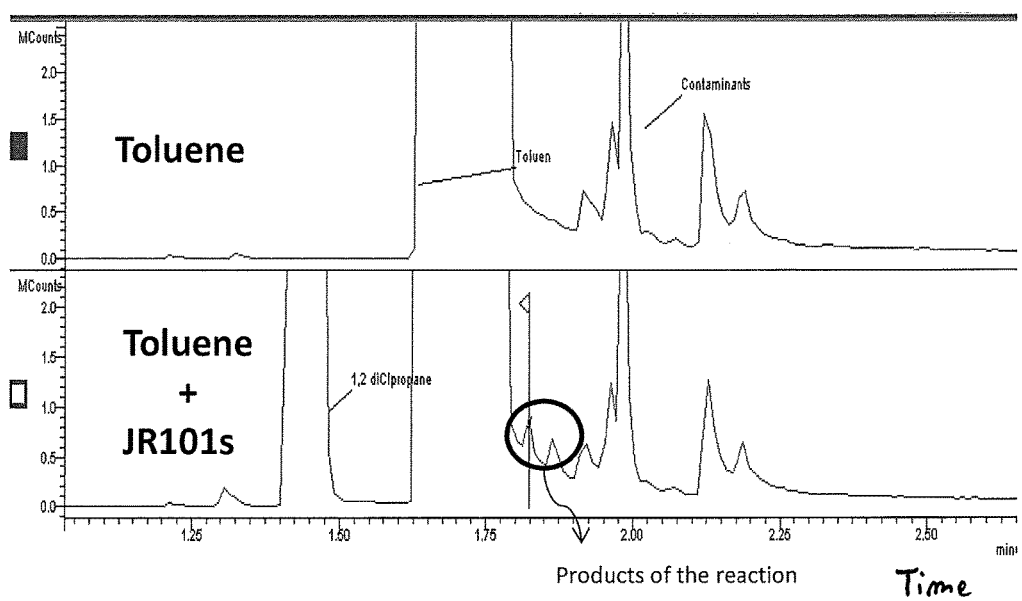

FIG. 23 shows a first representation of the chromatogram of the reactives (1,2 dichloropropane and toluene) and of the compound of the present invention (JR101s).

Figure 24:
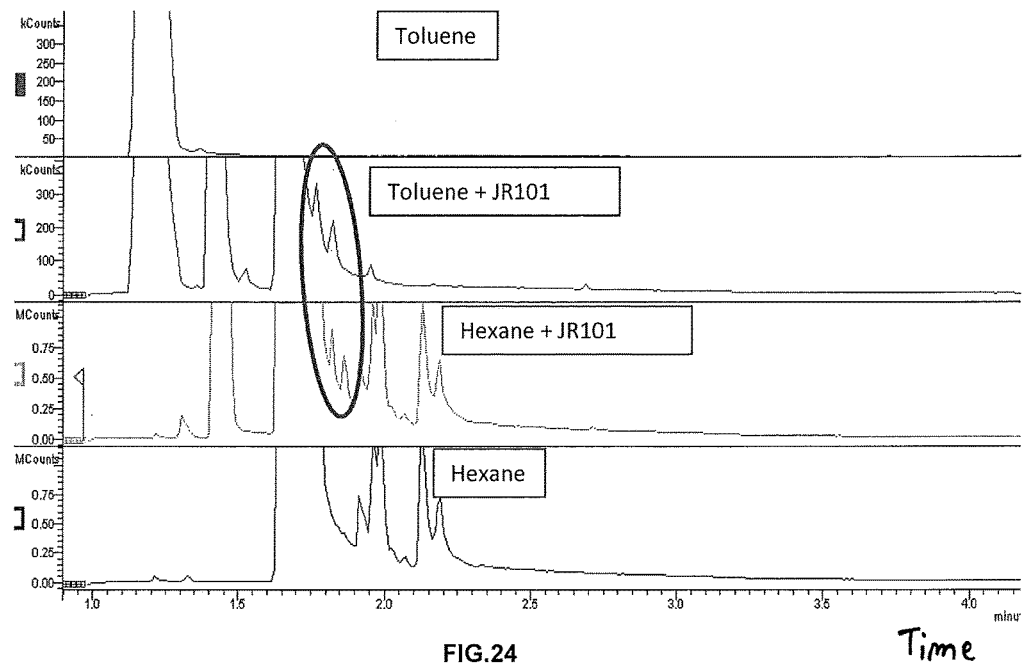

FIG. 24 shows a second representation of the chromatogram of the compound of the present invention (JR101s).

Figure 25:
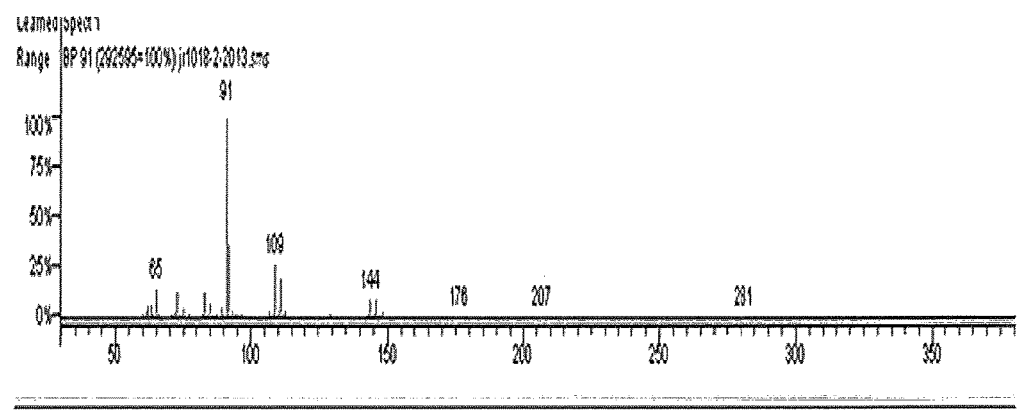

FIG. 25 shows a mass spectrum of the compound of the present invention (JR101s).

Figure 26:
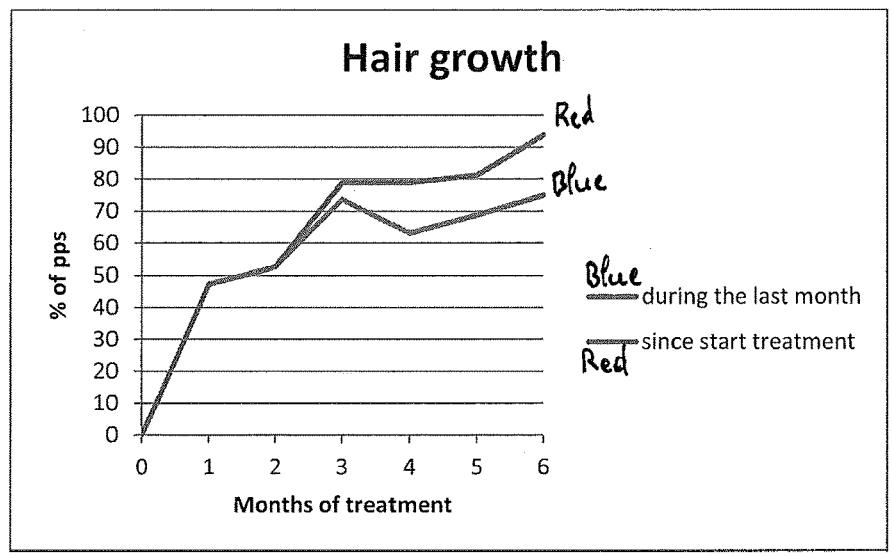

FIG. 26 represents a diagram showing the hair growth during the months (e.g. after 1 month 47% of patients using the cream of the present invention noticed new hair growth).

Figure 27:
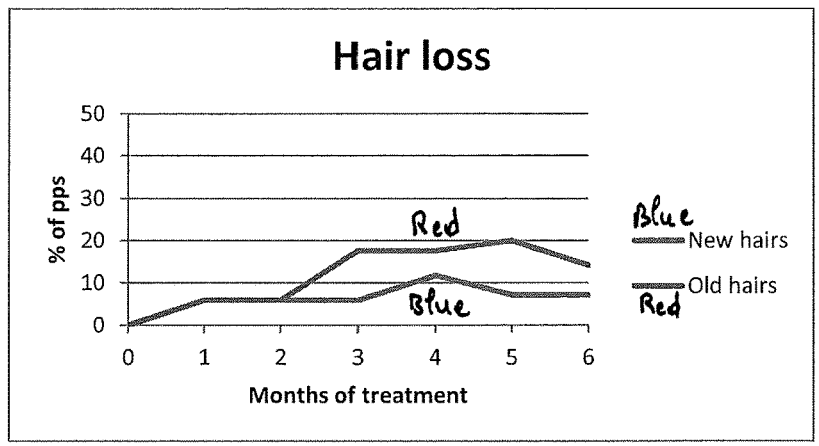

FIG. 27 represents a diagram showing the hair loss during the months.

Figure 28:
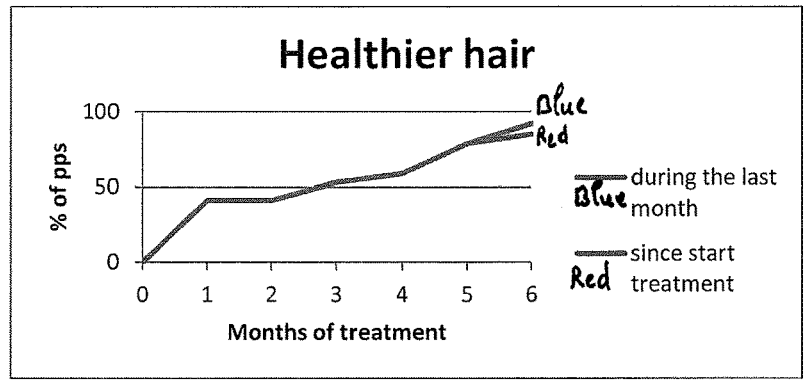

FIG. 28 represents a diagram showing the healthiness of hairs during the months.

Figure 29:
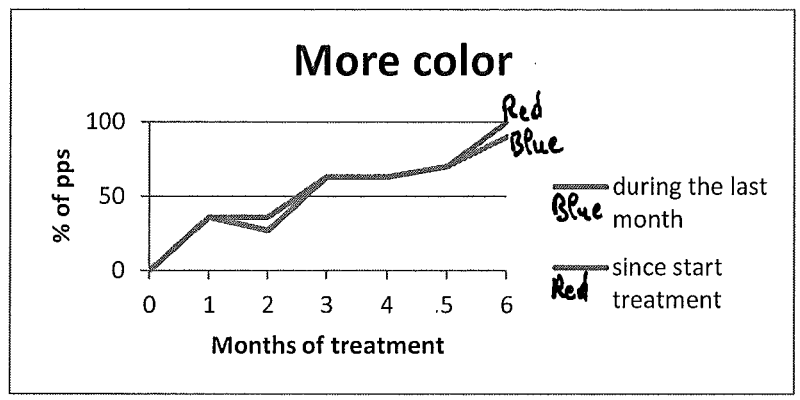

FIG. 29 represents a diagram showing the increase in hair colour during the months.

Figure 30:
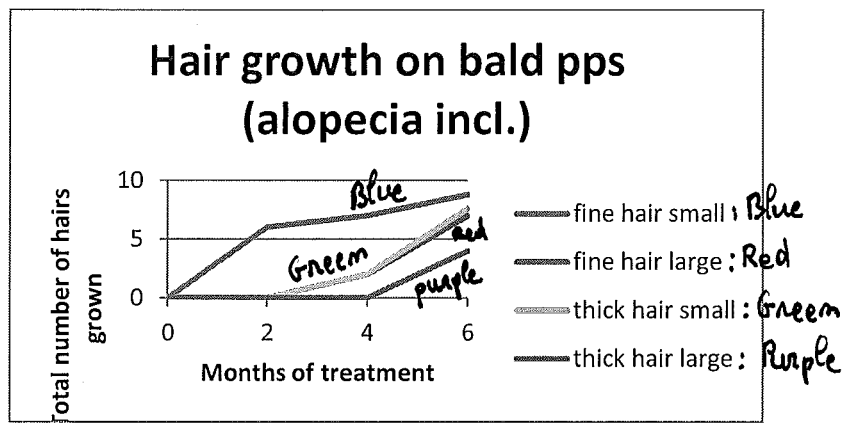

FIG. 30 represents a diagram showing the hair growth on bald patients during the months.

Figure 31:
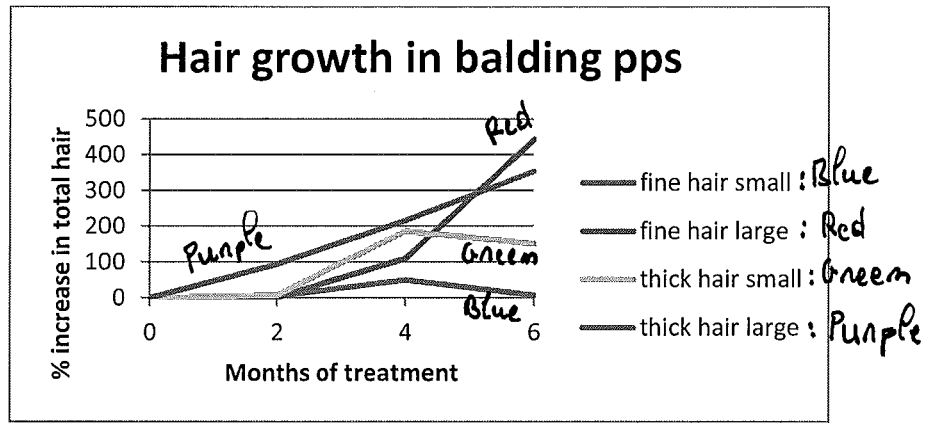

FIG. 31 represents a diagram showing the hair growth in balding patients during the months.

Figure 32:
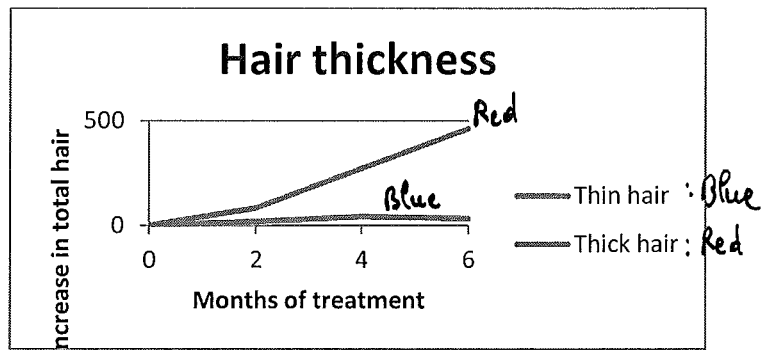

FIG. 32 represents a diagram showing the hair thickness during the months.

Figure 33:
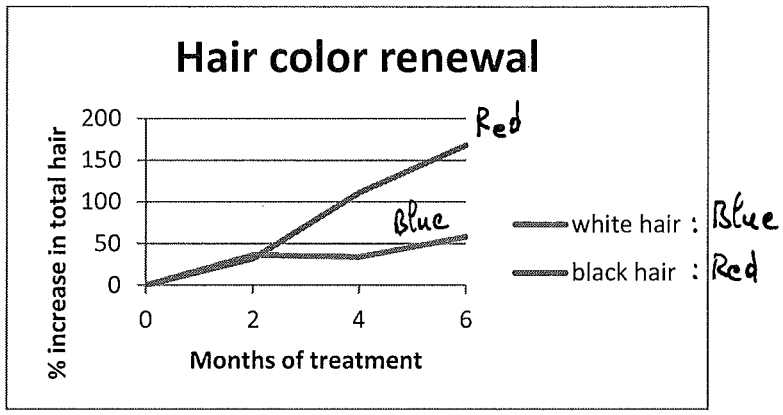

FIG. 33 represents a diagram showing the hair colour renewal during the months.

DETAILED DESCRIPTION OF THE INVENTION

The compound according to the present invention is the 3,6,6-trimethyl-5-(propan-2-yl)bicyclo[3.1.1]hepta-1,3-diene (JR101s) of Formula (I).

The compound according to the invention is an anti-Bredt compound which appears to be obtainable by chemical reaction and to be stable at room temperature.

The present invention relates to a chemical compound, a pharmaceutical compound or a pharmaceutically acceptable salt thereof and a cosmetic compound having the Formula (I):

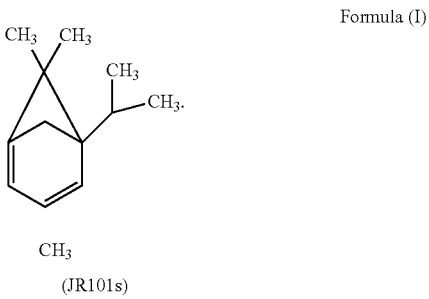

(JR101s)

The compound of Formula (I) is used (ex vivo) in treating the skin of a patient against heat and chemical burns or scalds.

The present invention also relates to a topical cosmetic/pharmaceutical composition (e.g. a cream) comprising a cosmetically/pharmaceutically acceptable vehicle and a dermatologically effective amount of a chemical compound having the Formula (I):

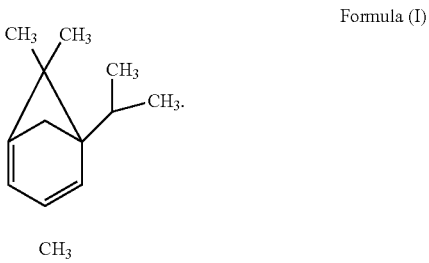

In another embodiment, the compound of formula (I) of the present invention increases collagen levels (anti-aging effect) in the body as well, so it can also be used as a medicament:

The present invention concerns a composition comprising a pharmaceutically effective concentration of a compound of formula (I) for use as a medicament.

The present invention concerns also a composition comprising a pharmaceutically effective concentration of a compound of formula (I) for use in curing and treating of heat (fire) and chemical (acid) burns or scalds (burns from heated fluids).

The present invention concerns a compound having the Formula (I) for use in medicine (as a medicament) namely for use in treating skin damages, i.e. against skin heat and chemical burns or scalds.

The present invention concerns also a compound having the Formula (I) for cosmetic use for hair growth.

The present invention concerns a composition containing at least a dermatologically effective amount of the compound of formula (I) and an acceptable vehicle (e.g. olive oil or jojoba oil). The present invention is not limited to olive oil and jojoba oil.

According to particular embodiments, the composition of the invention comprises one or a suitable combination of any of the following characteristics:
the composition of the present invention can comprise/contain 0.1% to 20% by weight, 0.2% to 19% by weight, 0.3% to 17% by weight, 0.4% to 16% by weight, 0.5% to 15% by weight, 0.6% to 14% by weight, 0.7% to 13% by weight, 0.8% to 12% by weight, 0.9% to 11% by weight, 1% to 20% by weight, 2% to 19% by weight, 3% to 17% by weight, 4% to 16% by weight, 5% to 15% by weight, 6% to 14% by weight, 7% to 13% by weight, 8% to 12% by weight, 9% to 11% by weight, 9% to 10% by weight, 10% to 11% by weight, 12% to 14% by weight, 0.1% to 30% by weight, 0.1% to 40% by weight, 0.1% to 50% by weight, 0.1% to 60% by weight, 0.1% to 70% by weight, 0.1% to 80% by weight, 0.1% to 90% by weight, 0.1% to 99% by weight, 1% to 20% by weight, 1% to 30% by weight, 1% to 40% by weight, 1% to 50% by weight, 1% to 60% by weight, 1% to 70% by weight, 1% to 80% by weight, 1% to 90% by weight, 1% to 99% by weight, 10% to 20% by weight, 10% to 30% by weight, 10% to 40% by weight, 10% to 50% by weight, 10% to 60% by weight, 10% to 70% by weight, 10% to 80% by weight, 10% to 90% by weight, 10% to 99% by weight of the dermatologically effective compound of formula (I) (JR101s).

Other appropriate ranges may also be the following: 0.001% to 0.01% by weight, 0.001% to 0.02% by weight, 0.001% to 0.03% by weight, 0.001% to 0.04% by weight, 0.001% to 0.05% by weight, 0.001% to 0.06% by weight, 0.001% to 0.07% by weight, 0.001% to 0.08% by weight, 0.001% to 0.09% by weight, 0.001% to 0.1% by weight, 0.001% to 0.2% by weight, 0.001% to 0.3% by weight, 0.001% to 0.4% by weight, 0.001% to 0.5% by weight, 0.001% to 0.6% by weight, 0.001% to 0.7% by weight, 0.001% to 0.8% by weight, 0.001% to 0.9% by weight, 0.001% to 1% by weight, 0.001% to 2% by weight, 0.001% to 3% by weight, 0.001% to 4% by weight, 0.001% to 5% by weight, 0.001% to 6% by weight, 0.001% to 7% by weight, 0.001% to 8% by weight, 0.001% to 9% by weight, 0.001% to 10% by weight, 0.001% to 11% by weight, 0.001% to 12% by weight, 0.001% to 13% by weight, 0.001% to 13% by weight, 0.001% to 14% by weight, 0.001% to 15% by weight, 0.001% to 16% by weight, 0.001% to 17% by weight, 0.001% to 18% by weight, 0.001% to 19% by weight, 0.001% to 20% by weight of the effective compound of formula (I).

The composition of the present invention comprises/contains 0.001% to 99.9% by weight, preferably 0.1% to 99.9% by weight, more preferably 0.1% to 50% by weight, most preferably 0.1% to 20% by weight, even more preferably 0.1% to 15% of the effective compound of formula (I).

The values of any range mentioned in the present invention can be combined with any other mentioned range to form a new range.

The acceptable vehicle of the composition of the present invention is selected from the group consisting of palmitic acid, palmitoleic acid, erucic acid, eicosenoic acid, docosenoic acid, oleic acid and linoleic acid.

The composition of the present invention is a topical anti-aging compound for application to the human skin defined to include in active form at least the following categories of anti-aging ingredients: DNA repair, cellular repair, anti-wrinkle, anti-redness, anti-pigment, anti-UV damage, anti-oxidant, barrier repair, emollient/moisturizer characteristics, pro-collagen, anti-abnormal skin lesions and UV damage reversal.

The composition of the present invention comprises:
Product A: compound of formula (I): 0.1% to 99.9% by weight
acceptable vehicle (base oil=e.g. jojoba oil or olive oil): 0 to 99.9% by weight
water: 0 to 99.9% by weight
emulsifier (Tefose® 2000): 0 to 50% by weight
propylene glycol: 0 to 99.9% by weight.

The preferred composition of the present invention comprises:
Product A: compound of formula (I) (diluted 100 times): 13% by weight
acceptable vehicle (base oil=e.g. jojoba oil or olive oil): 7% by weight
water: 57% by weight
emulsifier (Tefose® 2000): 3% by weight
propylene glycol: 20% by weight.

The composition of the present invention can be used for lifting up the levels of collagen and elastin in the skin.

The cosmetic composition of the present invention can be cosmetically used for hair growth.

The therapeutic composition of the present invention can be used for skin rejuvenation and skin repair.

The composition of the present invention can be cosmetically/therapeutically used for the nail rejuvenation and repair.

The composition of the present invention can repair nail damages made by a nail fungus and can also therapeutically treat the nail by destruction of the fungus.

The composition of the present invention can be used as a cream which is used for cosmetic and/or therapeutic use.

The present invention concerns a therapeutic/cosmetic cream containing the compound of formula (I).

The application of the composition of the present invention is to be considered as a cosmetic application/use (hair and nail growth) but also as a therapeutic treatment (skin and nail rejuvenation and skin and nail repair including fungal damage) of the human body which involves a therapeutic aspect due to the prophylactic effect which is indissolubly linked to the cosmetic use.

The present invention concerns also a method for therapeutically prevent or treat skin damages disease like heat and chemical burns or scalds on a human or animal patient comprising:
administering to the patient in need thereof a composition comprising 0.1% to 99.9% by weight of the compound of formula (I), 0 to 99.9% by weight of a base oil (e.g. jojoba oil or olive oil), 0 to 99.9% by weight of water, 0 to 50% by weight of Tefose® 2000 (emulsifier), 0 to 99.9% by weight of propylene glycol.

Synthesis of the Compound of Claim 1:
The person skilled in the art would know how to manufacture the compound of the present invention thanks to the following information.

The experimental manufacturing example which follows is illustrative and does not restrict the scope of the invention.

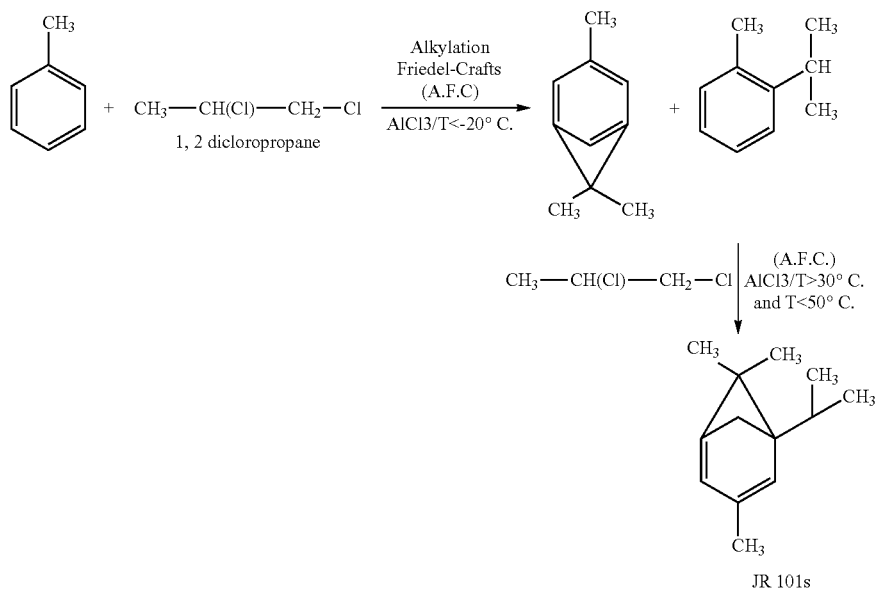

JR 101s

Essential features:
adding AlCl3 to 1, 2 dicloropropane at 4° C. = product 1 (carbocation)
After 30 minutes add product 1 to toluene at 4° C. and pass very soon
(1minute) to -80° C. and incubate 30 minutes = product 2 (intermediate product)
Product 2: it must follow 5 times (minimum) the change of temperature:
From -80° C. where it was 30 minutes to 40° C. and incubated 30 minutes
After that from 40° C. to -80° C. (30 minutes)
The end product JR101s is stable at room temperature.

C13H20
3, 7, 7 trimethyl-6
(propan2yl) bicyclo
[4.1.0]hepta 1, 3 diene

It appears that a highly strained compound could be formed with sufficiently energy-rich precursor reacting irreversibly and in only one direction available, and that its isolation can be successful if no subsequent reactions occur.

The probable reaction mechanism of the chemical reaction occurring during Friedel-Crafts alkylation could be drawn as the following scheme.

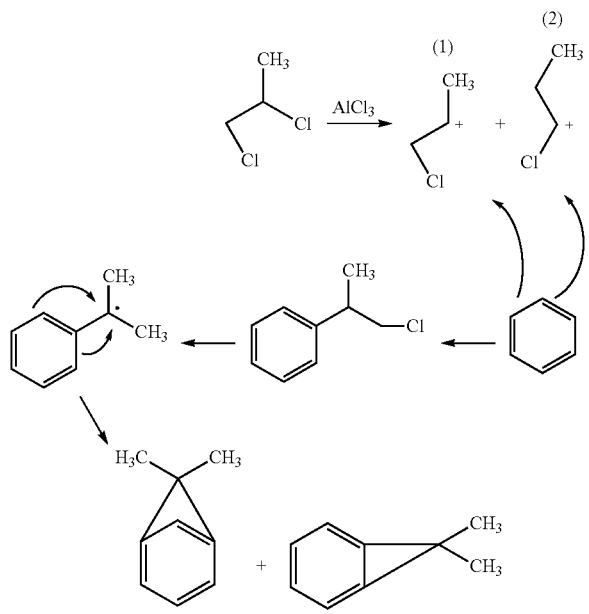

The reaction of 1,2-dichloroalkanes with the benzene moiety leads to two carbocation (1) and (2), the most stable being (1), so that the major 1-chlorophenylalkane obtained is the one shown in scheme 2.

It appears that the reaction conditions used, especially the cycle of several (at least five) variations of reaction temperature and time as mentioned in the synthesis of the compound of the present invention (see essential features of the synthesis) allows forming the compound of formula (I) according to the invention.

The compound thus obtained was characterized by Mass Spectrometry by diluting the compound in organic hydrophobic solvents, such as: hexane and toluene, solvents also used as references in mass spectrometry analyses. For example, FIG. 20 represents the chromatogram obtained for toluene, the arrow corresponding to the elution of toluene from the column and other peaks corresponding to contaminants and FIG. 21 represents the mass spectrum of toluene.

FIGS. 22 to 25 represent the chromatogram and the mass spectrum of the compound according to the invention.

The compound was quantified according to reactive consummation and the results according to area and height of each compound tested are given in Table 1, in which Index 3(3) corresponds to 1,2-dichloropropane, Index 5(5) corresponds to toluene, Index 6(6) and Index 7(7) correspond to the products of the reaction.

Mass Spectrometry Spectrum:

In order to carry out the chemical characterization of the compound of the present invention (i.e. the JR101s compound of formula (I)) a mass spectrometry has been made using organic hydrophobic solvents such as: hexane and toluene. Also the solvents were used as references in mass spectrometry studies.

Samples preparation: the compound of the present invention (JR101s) was diluted in hydrophobic solvents and shown in FIG. 20, the chromatograms and spectra were obtained for the toluene compound.

Toluene was characterized by mass spectrometry and the results are shown in FIG. 21. In FIG. 22 the characterization of the product reaction involved in the JR101s synthesis is shown.

Thus, with benzene (about 99% pure) a JR101s production has been made and the spectra of reactives and products in the production of JR101s are shown in FIG. 23.

The "Products of the reaction" were quantified with reactive consummation and the Table 1 shows results according to area and height of each compound tested.

TABLE 1

Representation of % of JR101s production.

| Index | Time | Area | Height | Results | Units |
|---|---|---|---|---|---|
| 1(1) | 1.172 | 28908582 | 12374897 | 14.87 | % |
| 2(2) | 1.229 | 7730397 | 5990304 | 3.977 | % |
| 3(3) | 1.418 | 34813348 | 31586832 | 17.91 | % |
| 4(4) | 1.525 | 58807 | 42741 | 0.030 | % |
| 5(5) | 1.650 | 122470144 | 80262648 | 63.01 | % |
| 6(6) | 1.767 | 131652 | 124777 | 0.068 | % |
| 7(7) | 1.825 | 139490 | 108874 | 0.072 | % |
| 8(8) | 1.955 | 49797 | 42902 | 0.026 | % |
| 9(9) | 2.691 | 15868 | 14469 | 0.008 | % |
| 10(10) | 20.075 | 11985 | 5212 | 0.006 | % |
| 11(11) | 20.371 | 10883 | 3151 | 0.006 | % |
| 12(12) | 20.460 | 12298 | 4057 | 0.006 | % |

Index 3(3) corresponds to 1,2-dichloropropane.
Index 5(5) corresponds to toluene.

Index 6(6) and Index 7(7) correspond to the products of the reaction.

Unit (last column) corresponds to the % of Molecular Weight of each reactive and product. We confirmed by mass chromatography the formation of JR101s (see FIGS. 24 and 25).

Thus, the compound according to the invention was identified and could be quantified.

The stability of the compound according to the invention was confirmed by calculations.

Calculation of the energy of the most stable isomer of the compound 3,6,6-trimethyl-5-(propan-2-yl)bicyclo[3.1.1]hepta-1,3-diene was performed using the DREIDING method as disclosed by Stephen L. Mayo et al in "DREIDING: A Generic Force Field for Molecular Simulation." *J. Phys Chem.* 1990, 94, 8897-8909.

Empirical force field calculations are the only computational methods which allow total optimization of all conformational isomers of larger molecules. They also give generally reliable geometries and energies where comparisons with experiment can be made. Moreover, such calculations also permit the ready examination of systems presently unknown, unavailable, inaccessible, or experimentally impossible. Empirical force field calculations refer to the ground state and only reflect thermodynamic stability.

According to the calculated olefin strain, OS, values, bicycle[1.1.1]pent-1-ene (2) of the table II of [4] is predicted to be observable while (10) might not. Regarding Wiseman rule "when the trans alkene-containing ring is seven or six membered, bridgehead olefins are predicted not to be observable at room temperature", (2) violated this rule. Which leads to the question "are these rules applicable to other types of strained olefins? Unfortunately, not always [4]." In our invention (10) will be an homolog of the compound 3,6,6-trimethyl-5-(propan-2-yl)bicyclo[3.1.1] hepta-1,3-diene, but not similar and then they cannot absolutely obey to the same rule. To support this assertion, we performed analysis of the compound 3,6,6-trimethyl-5-(propan-2-yl)bicyclo[3.1.1]hepta-1,3-diene on the website chemicalize.org.

The site gives us the properties of compound 3,6,6-trimethyl-5-(propan-2-yl)bicyclo[3.1.1]hepta-1,3-diene as listed below.

Figure 11:
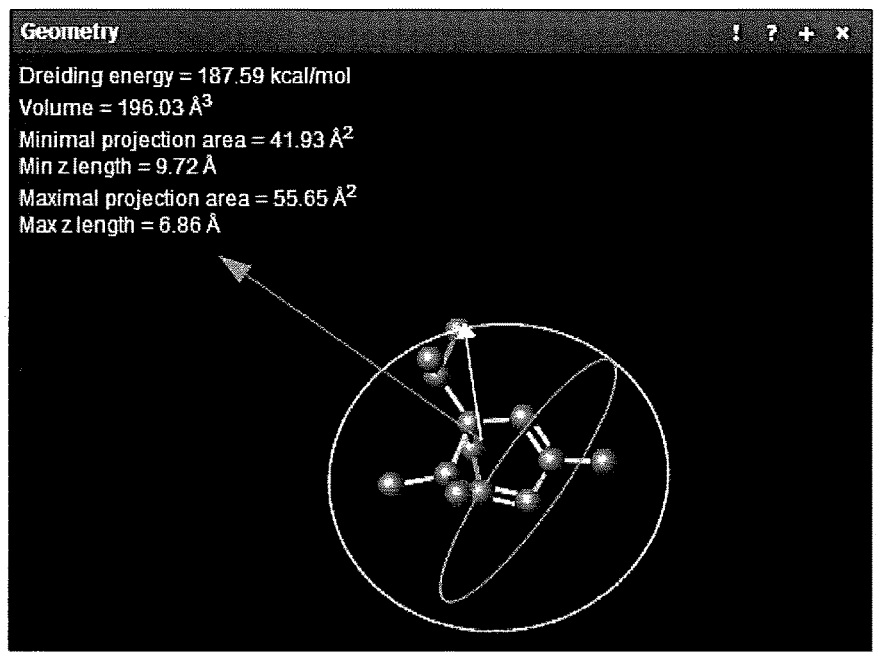
FIG. 11 represents the modelization of 3,6,6-trimethyl-5-(propan-2-yl)bicyclo[3.1.1]hepta-1,3-diene (the compound of formula (I) of the present invention).

The properties of 3,6,6-trimethyl-5-(propan-2-yl)bicyclo [3.1.1]hepta-1,3-diene were studied using the modeling tool provided by website chemicalize.org (http://www.chemicalize.orq/structure/#!mol=C1C %28C %3DC %28C2%29C %29%28C %28C %29C %29C %28C1%3D2%29%28C %29C&source=calculate), which gives its stability energy (187.59 kcal/mil) and which also gives a geometrical representation of the molecule (see FIG. 11). This modeling shows also that the molecule haven't asymmetric distribution of electron which is generally observed in bridgehead molecules due to the strain on the double bound as it could be expected as the bridgehead carbon becomes more electron deficient as the olefin becomes more strained, while the exocyclic carbon gains electron density, thus polarizing the bond. Once has to notice that the surface tension of the compound is reduced by alkyl groups related to the decrease of entropy changes associated with molecules in the low molecular weight as disclosed by S. Bartlett et al. in "Configurational stability of bisindolylmaleimide cyclophanes: from conformers to the first configurationally stable, atropisomeric bisindolylmaleimides". *Chemistry.* 2005 Oct. 21; 11(21):6277-85 and by Li C et al. in "Molecular dynamics study of the molecular weight dependence of surface tensions of normal alkanes and methyl methacrylate oligomers". *J Phys Chem B.* 2006 Apr. 6; 110(13):6864-70 and Curcio, N. M. et al. in "Injectable fillers: An American perspective". *Giornale Italiano di dermatologia venereologia*, 3, 271-279(2009). Surface tensions (gamma) of 3,6,6-trimethyl-5-(propan-2-yl)bicyclo[3.1.1]hepta-1,3-diene (JR101s) normal alkane alkyled with low molecular weight was computed using a newly proposed molecular dynamics (MD) simulation strategy which was developed based on the definition of gamma=(partial differential U/partial differential sigma) n,V,S.

As well, 3,6,6-trimethyl-5-(propan-2-yl)bicyclo[3.1.1] hepta-1,3-diene (JR101s) steric effect are leading to large differences in configurational stability. The orientations of the alkyl group towards cyclohexane lead to get stable 3D conformation.

The stability of the compound according to the invention, alone or incorporated in a topical preparation, has being evaluated (FIG. 11) using High Performance Gas Chromatographic (HPGC) under the variation, temperature and time conditions mentioned in the synthesis scheme of the compound of formula (I) of the present invention, and the results show that the compound is stable over the time at room temperature.

In conclusion, when calculating the Drieding energy of the most stable isomer of the compound 3,6,6-trimethyl-5-(propan-2-yl)bicyclo[3.1.1]hepta-1,3-diene, it becomes evident that the compound of the present invention remains stable at room temperature. Therefore, the compound of formula (I), the composition and the cream of the present invention are stable at room temperature.

Examples

Example 1

The efficacy of a cosmetic composition according to the invention was assessed by a clinical trial run by a medical esthetics company named Sempervivum.

Twenty-four volunteers (22 women and 2 men) participated in this study. Participants were on average 59 years old (Mean (M)=59 years, Standard Deviation (SD)=12 years). For clarification (M) stands for Mean (all ages added up and divided by the number of participants) and (SD) means Standard Deviation (Square root of the variation). It is always mentioned in scientific papers when scores/ages are given. In this case, the age of the participants is 59 years with an average deviation of 12 years.

Participants had no history of cosmetic surgery and stated to have normal eating and sleeping patterns.

In order to scientifically assess the skin elastin and collagen levels of the skin, the DermaLab Combo was used (Cortex Technology, Denmark 2010). The DermaLab Combo offers high precision and reproducibility on all its measuring parameters of the skin, making it ideal for comparison over time. A built-in client database makes it easy to recall previous recordings and compare with new measurements. The DermaLab combo has a separate probe for measuring the elasticity and collagen fibers of the skin. Moreover, it is the only ultrasound device that allows accurate collagen measurements that are unparalleled in similar product lines in the world.

The collagen probe of the DermaLab® is a high-resolution ultrasound scanner dedicated to skin applications. It provides cross-sectional images of the dermis (see FIG. 1), which clearly show the alteration of the collagen fiber matrix as result of photo-ageing and it can demonstrate how this process can be reversed by stimulating the production of natural collagen. When administering the collagen probe to the skin, an ultrasound picture of the skin is taken and based on the light reflections in this picture an estimate of the total amount of collagen in that part of the skin is given as an intensity score. Ultrasound skin imaging is based on measuring the acoustic response from the skin, when an acoustic pulse is sent into the skin. The energy of the acoustic pulse is very low and does not affect the skin in any way. When the transmitted acoustic pulse hits the different borders in the structures of the skin a part of the transmitted pulse will be reflected and the signal will travel back and be picked up by the ultrasound probe. The precision of the collagen score measurement with the DermaLab® on the same position on the skin is within 5%. The cross-sectional images represent an intensity (amplitude) analysis of these returned signals. The intensity of the received signal refers to a color scale, where dark colors represent areas of the skin with low reflection (i.e. none or small changes in density between the structures in the skin) and bright colors represent areas with strong reflections (i.e. significant changes in density between structures). Typically the epidermis gives a high intensity (white/yellowish) and the dermis a mix of many colors. The collagen score is calculated as the average intensity (=rectified amplitude) from the received ultrasound signal inside the area of dermis (or alternatively inside the "red-grid" area defined by the red-grid left/right cursors). This measurement is based on a large line of research relating ultrasound skin imaging to, collagen levels (De Rigal et al., 1989 Assessment of aging of the human skin by In vivo ultrasonic imaging. *J Invest Dermatol.* 93, 621-625). The intensity on the DermaLab® measures has a range of 0-255, where levels over 150 are practically not achievable because the dermis can never give such a strong response (it would be an all-bright image). The collagen score is therefore divided by 1.5 and truncated at 100. Typical scores range from 5 to 65 points. An increase in intensity scores of 10 points as a result of cosmetic products is considered as a large therapeutic effect.

The elastin probe of the DermaLab® is a suction cup elasticity probe. In order to ensure un-biased readings, the DermaLab® features a light weight probe which, when glued to the skin using a double adhesive sticker, eliminates movement artefacts from holding the probe. The unit allows for adjusting the airflow according to the measurement site and actual skin condition. With the probe in place, negative pressure will elevate the skin, and the differential negative pressure needed to lift the skin a predetermined distance is used as input to calculate Young's modulus (E). Two additional parameters are presented to describe the skin elasticity: the retraction time (R) and the viscoelasticity (VE), a parameter combining both the elevation and retraction phase in one number. Both, the (VE)-score and the (E)-score are functional parameters for the skin's elasticity.

The topical composition comprising the compound according to the invention was prepared according to following protocol. 40 mL of JR101s were added to 4 liters of oil (jojoba or olive oil) given "product A". The product A is a dilution 1/100 of JR101s that is under maceration (optional) during 2-3 weeks. (Agitation 5 minutes every day of the mix). The product A after maceration comprises two phases (oil+aqueous), the oil phase was recovered. After analysis, it appears that 90% of total JR101s synthesized is present in the oil phase.

The composition of the topical preparation is given in table 2.

Participants were explained how to apply the cosmetic product. Each participant applies the product two times a day and do not to use any other cosmetic products for the duration of the study other than a neutral lotion. A picture was taken of each participant's face, one frontal picture and two sideways pictures (left and right). Then collagen and elastin levels were measured by means of the DermaLab® Combo. The participants were given a jar of the cosmetic composition (50 ml), a supply that would be sufficient for a month's time. After each month the participant had to return for another set of facial pictures and measurement of elastin and collagen levels as well as to receive additional cream.

The measurement always started with the ultra-sound probe for testing the collagen levels. Collagen levels were tested at three different places on the skin, one at the forehead, one at the cheek, and one at the chin. The probe was placed at the specific part of the skin and an ultrasound picture was taken. The obtained picture of the skin as well as the collagen intensity score was stored on the machine. Thereafter, elastin levels were measured using the elasticity probe, on two places of the skin, namely the cheek and the chin. The suction cup was attached to the skin and expanded by the pumping mechanism of the DermaLab®. The different elasticity scores were stored on the machine. These measures were used for the data analysis.

Example 2

For analytical reasons participants were divided into four different age groups. In the first group participants were younger than 55 years of age; in the second group participants had an age comprised between 55 to 64 years. In the third group they had between 65 and 74 years of age and in the fourth group they had over 75 years of age.

To assess collagen levels, 5 measures were performed (Time of measurement: start, 1 month, 2 month, 3 month, 4 month) at three skin locations (measurement area: front, cheek, chin) repeated with measures analysis of variance (ANOVA) with collagen score as the dependent variable. Importantly, there was a significant main effect of Time in a F-test, $F(4,92)=8.91$, $p<0.001$. More specifically, there was a significant linear trend, $F(1,23)=55.91$, $p<0.001$. Indeed in a statistical analysis a specific test has to be performed, the F-test, generally used to analyze the main effects. It analyses the average score in one particular group (in the present case the scores at the beginning) and how they differ from another group. By doing this for several groups (in this case the scores at the beginning of month 1, month 2 etc.) you use the F-test which returns a specific value.

IF the value is 0 there is no effect. The values 4 and 92 indicate the variability degrees of the test itself. Important is to know that the p-value is a kind of probability score. What is done with the F-test is to see how large the probability is to obtain these scores if there is no improvement. A p-value of 0.05 means there is a 96% chance that the scores of a participant between the time of measurement 1 and the time of measurement 2 will be different.

It is generally accepted that the effect is significant when the p-value is smaller than 0.05. $p<0.001$ means that we have a 99.9% chance the scores are higher with subsequent measurements (later than previous ones). All of these are clearly the case in the present invention.

Participants' collagen scores were significantly higher after four months of application of the cream (Mean Elasticity score (Mes)=41.9, Standard Deviation (SD)=3.6), than at the start of the trial (Mean Elasticity score (Mes)=28.1, Standard Deviation (SD)=1.6). For clarification, (Mes) is the average collagen intensity score and (SD) the average deviation thereof. Mean collagen scores averaged over all the probed areas were increased by four points after one month of cream use, eight points after two months, fourteen points after three months and by fifteen points after four months.

The main effect of measurement area also reached significance, $F(2,46)=18.95$, $p<0.001$. Collagen scores were higher at the chin region (Mean Elasticity score (Mes)=45.3, Standard Deviation (SD)=2.8), than at the front or cheek (front: Mean Elasticity score (Mes)=29.6, Standard Deviation (SD)=1.3; cheek: Mean Elasticity score (Mes)=33.9, Standard Deviation (SD)=1.8). The interaction effect of time×place however was not significant, $F(8,184)=0.97$, $p=0.46$, providing evidence that the cream had effects in the same direction on all places of the face. The mean scores for the different areas can be found in Table 2.

Figure 3:
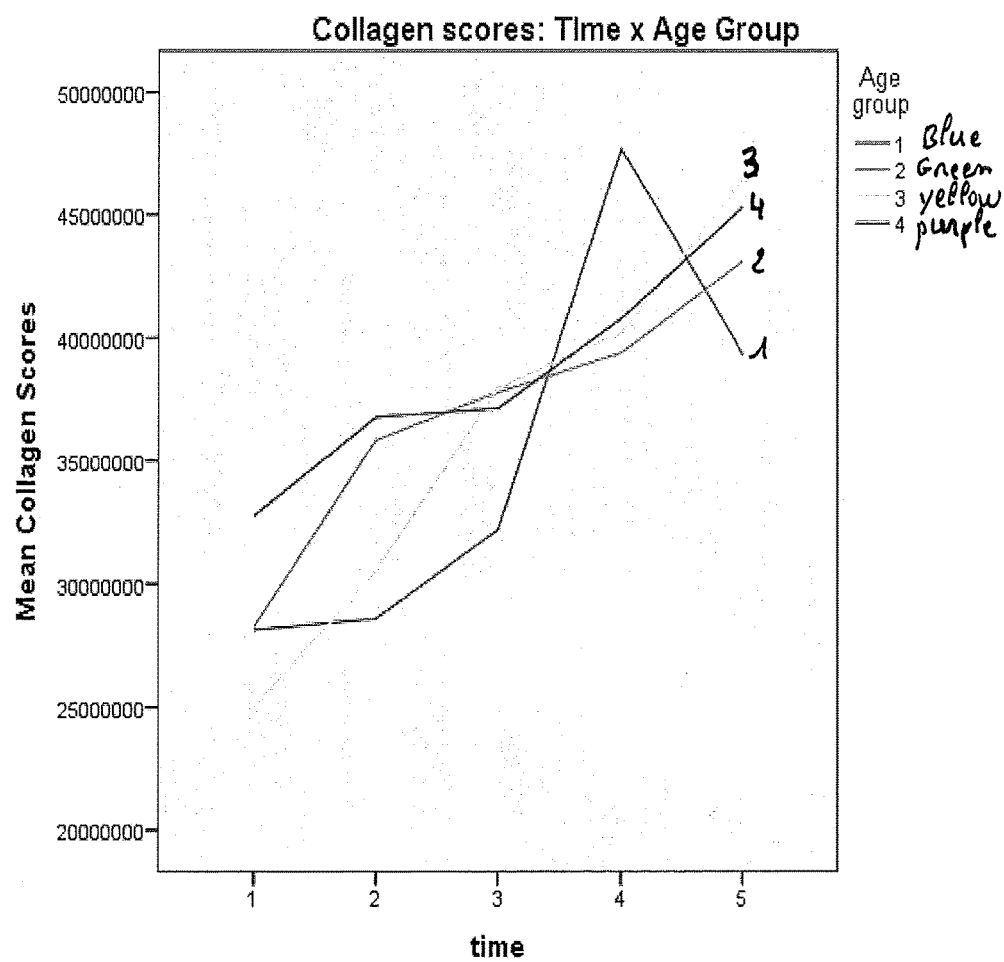
FIG. 3 represents the mean collagen scores as a function of the variables Time and Age Group.
Figure 4:
FIG. 4 represents the camphane and pinane ring systems of document D1.
Figure 5:
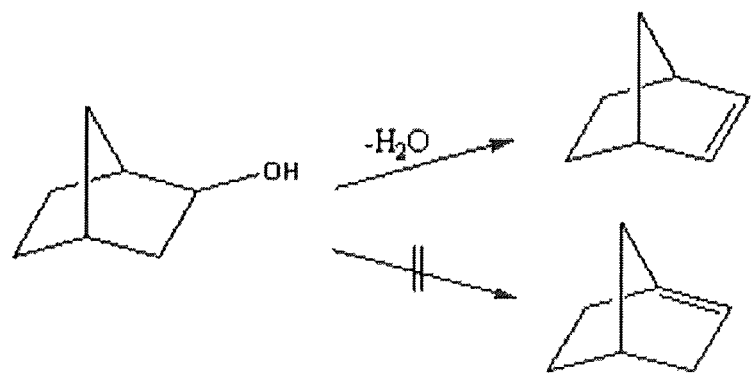
FIG. 5 represents a first illustration of the Bredt's rule of document D1.
Figure 6:
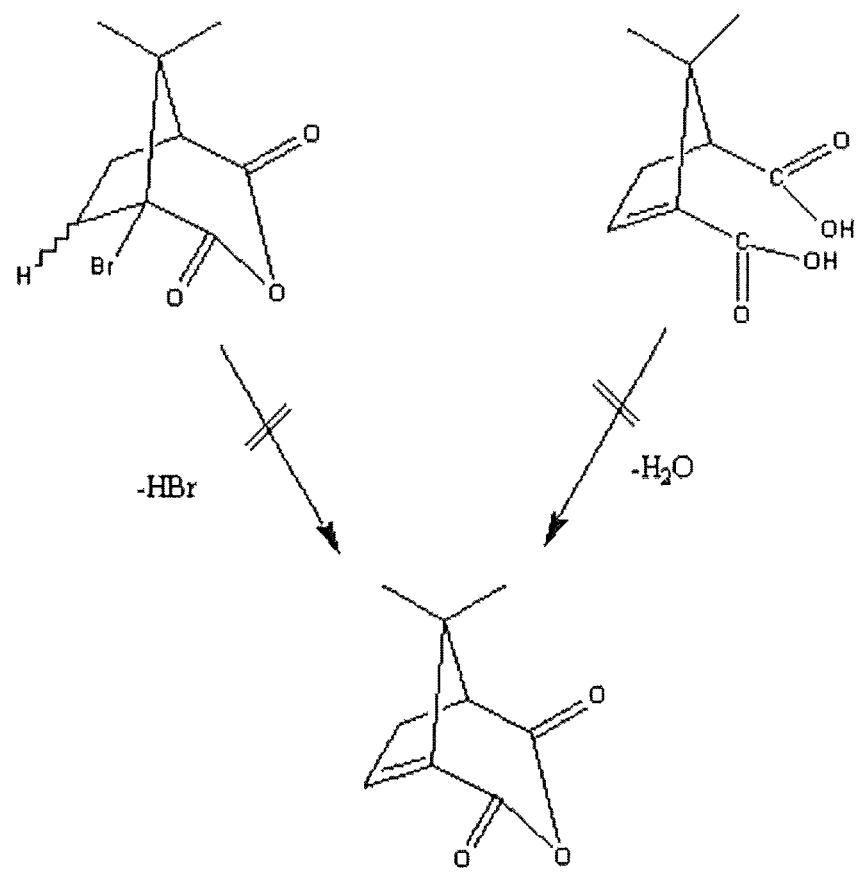
FIG. 6 represents a second illustration of the Bredt's rule of document D1.
Figure 7:
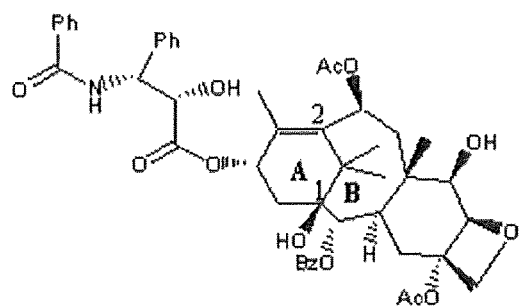
FIG. 7 represents the taxol molecule and a bicyclic compound of the [5.3.1] type of document D1.
Figure 7:
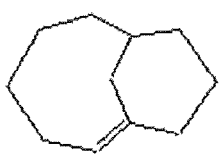
Figure 8:
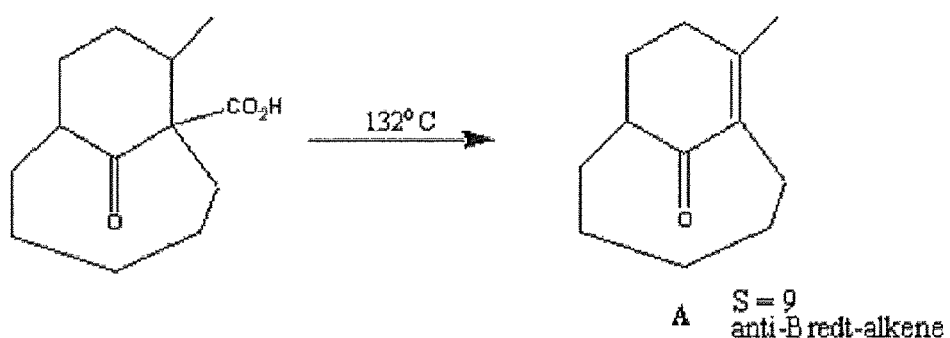
FIG. 8 represents a b-ketoacids decarboxylation (document D1).
Figure 8:
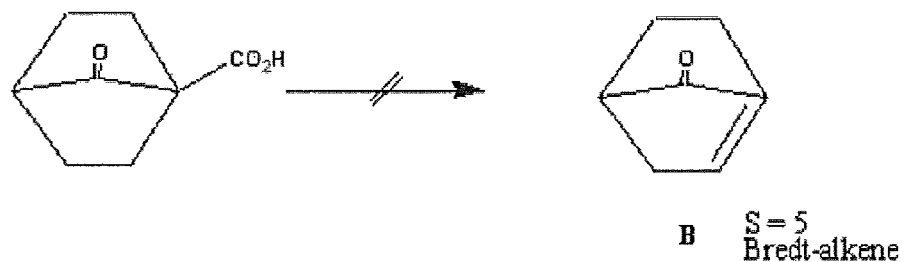
Figure 9:
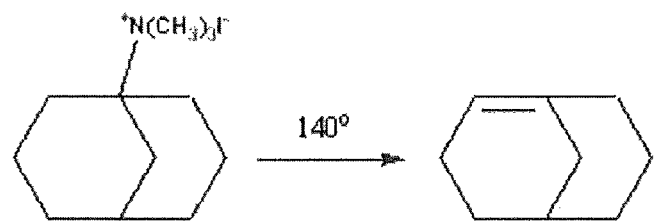
FIG. 9 represents a reaction scheme for forming bicyclo [3.3.1]non-1-ene.
Figure 10:
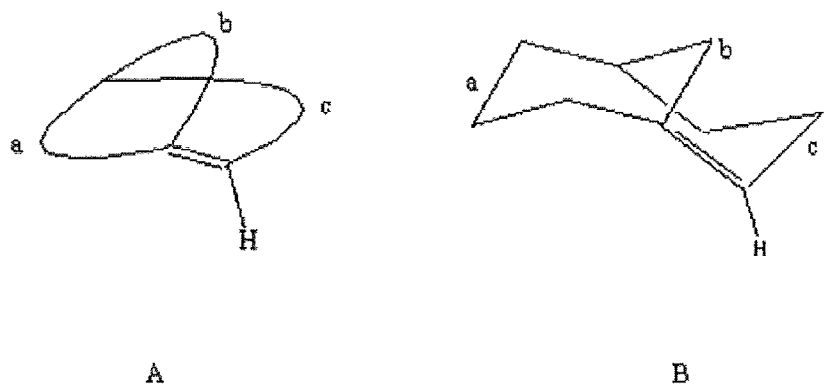
FIG. 10 represents a generic cycloalkene (A) and bicyclo [3.3.1]non-1-ene (B).

Subsequently an ANOVA was performed in which we included the age group variable was included as a between-subjects factor. The effect of time remained significant, $F(4,80)=6.71$, $p<0.001$. However, there was no main effect of Age Group, $F(3,20)=0.19$, $p=0.90$. Participants did not have significantly lower collagen scores depending on their age. This might be due to the low number of participants and heterogeneity in the samples. There was no interaction effect of Time×Age group (see FIG. 3), nor any other significant interaction effects, Fs<1, ps>0.50. The Time effect however was significant in all four of the age groups, showing that, although there were slight differences in the scores, the therapy was efficient for all samples.

To assess skin elasticity, 5 measures were performed (time: start, 1 month, 2 month, 3 month, 4 month) at two skin area (measurement area: chin, cheek) repeated two times (score: E, VE) with repeated measures analysis of variance (ANOVA) on the elasticity scores. Importantly, there was a significant main effect of time, $F(4,96)=8.02$, $p<0.001$. Again a significant linear trend was observed, $F(1,24)=27.87$, $p<0.001$. Elasticity scores were significantly higher after four months of application of the topical preparation (cream) (Mean Elasticity score (Mes)=3.55, Standard Deviation SD=0.3), than at the start of the trial (Mean Elasticity score (Mes)=2.75, Standard Deviation SD=0.3). Mean elasticity scores averaged over both the probed areas were increased by 0.3 points after one month of topical preparation (cream) use, by 0.7 points after two months, 0.7 points after three months and by 0.8 points after four months.

There was also a significant main effect of score, VE-scores are lower than E-scores. However, there was no main effect of place. More importantly, the interaction effect of time×place was not significant and neither was the three-way interaction effect, ps>0.50. The mean scores for the different areas can be found in Table 3.

TABLE 2

In table 2, are given Mean Collagen scores (and standard deviations) at the beginning of the study and after one, two, three and four months for the different measurement areas.

|  | Start | | 1 Month | | 2 Months | | 3 Months | | 4 Months | | Difference | |
| --- | --- | --- | --- | --- | --- | --- | --- | --- | --- | --- | --- | --- |
|  | Mes | SD | Mes | SD | Mes | SD | Mes | SD | Mes | SD | Mes | SD |
| Front | 23 | 2 | 28 | 4 | 29 | 3 | 32 | 3 | 36 | 4 | 13* | 3 |
| Cheek | 27 | 2 | 29 | 2 | 35 | 4 | 37 | 3 | 42 | 5 | 15* | 3 |
| Chin | 35 | 2 | 39 | 4 | 43 | 4 | 59 | 3 | 59 | 6 | 15* | 4 |

*Significant with p < 0.05
"Mes" stands for "Mean Elasticity score"
"SD" stands for "Standard Deviation"

TABLE 3

In table 3, are given Mean Elasticity scores and standard deviations at the beginning of the study and after one and two months for the different measurement areas.

|  | Start | | 1 Month | | 2 Months | | 3 Months | | 4 Months | | Difference | |
|---|---|---|---|---|---|---|---|---|---|---|---|---|
|  | Mes | SD | Mes | SD | Mes | SD | Mes | SD | Mes | SD | Mes | SD |
| VE-Cheek | 0.8 | 0.2 | 1.2 | 0.4 | 1.3 | 0.1 | 1.2 | 0.3 | 1.3 | 0.4 | 0.5 | 0.3 |
| E - Cheek | 4.4 | 1.1 | 4.6 | 1.0 | 5.2 | 1.0 | 5.1 | 0.6 | 5.5 | 0.9 | 1.1* | 1.0 |
| VE - Chin | 0.7 | 0.1 | 0.8 | 0.2 | 1.1 | 0.3 | 1.1 | 0.1 | 1.1 | 0.3 | 0.4 | 0.2 |
| E - Chin | 5.1 | 0.9 | 5.4 | 1.0 | 6.1 | 1.3 | 6.1 | 1.0 | 6.3 | 1.2 | 1.2* | 1.1 |

*Significant with $p < 0.05$
"Mes" stands for "Mean Elasticity score"
"SD" stands for "Standard Deviation"
(E) is the Young's modulus.
(VE) is the viscoelasticity.

In accordance with the analysis of the collagen scores, an ANOVA was performed using in which we used the age group variable as a within-subjects factor. The effect of time was again significant, $F(4,84)=8.56$, $p<0.001$. There was no main effect of Age Group, $F(3,21)=1.78$, $p=0.18$. Participants did not have significantly lower elastin scores depending on their age. This might be due to the low number of participants and heterogeneity in the samples. Importantly, there was no interaction effect of Time×Age group, $F(12, 84)=0.87$, $p=0.58$. The intervention had no differential effect related to the age of the participants.

Figure 1:
FIG. 1 represents a high-resolution ultrasound scanner image of a skin structure suffering of photo ageing where disorganized collagen appears as dark areas in the upper dermis.
Figure 2:
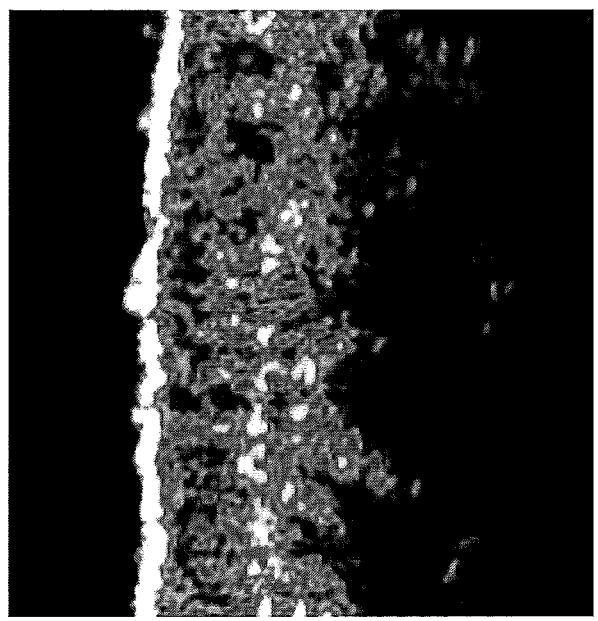
FIG. 2 represents a high-resolution ultrasound scanner of a skin treated by the compound according to the invention, wherein the collagen matrix has an increased intensity and the skin having a smoother surface.

Pictures of the skin collagen are shown in FIG. 1 and FIG. 2. In line with the data, the images after treatment show significant increased intensity. It appears that more interconnected collagen fibres are present in the dermis of the skin. Also, spots representing collagen seem to be more connected and closer to the epidermal layer.

A decline in facial wrinkles is expected but could not be precisely assessed using in the facial pictures of the participants. More studies should be performed.

Hair growth was also assessed on a 85 years old participant to the study suffering from hair loss and thinning hair. The person applied the topical preparation (cream) on the base of the scalp on her forehead for 6 months. Subsequent analysis showed the return of healthy and thick hair after already 3 months.

Men with DHT caused by hair thinning applied a spray of the composition of the present invention (JR101) during 2 months on the thinning area of the back of the scalp. Hair started to grow thicker and more abundant after 2 months.

Skin burn was assessed on a lab technician who burned both hands. One hand was treated during one month with the composition of the present invention (JR101), and the other not. After one month the hand treated with JR101 developed new smooth skin. The other untreated hand developed calluses instead.

Discussion

In a four-month study collagen and elastin levels in the skin were investigated together with the effectiveness of the compound of the present invention (JR 101) in a topical composition (cream) on these levels. Results imply that the topical composition is highly effective in stimulating collagen and elastin levels in the skin on a number of different places in the face. The effects on the skin seem to persist at least throughout the two first months and seem to be observed for all different age groups. The effects on the collagen levels after two months are in the order of 8 intensity points, be it a 30% increase in collagen compared to baseline. After four months the increase was up to 15 points or a 55% increase in collagen compared to baseline. The effects on elastin levels after two months are in the order of 0.7 elasticity points, be it a 25% increase in elastin compared to baseline. After four months the elastin levels were raised by 28% compared to baseline.

The effect of the topical composition on wrinkle reduction should follow from this increase in elastin and collagen levels. This should start immediately when starting the treatment, however as the collagen fibres are build up in the skin, it will take some time for those fibres to connect and reach the surface of the skin. A large effect on the skin should be evident after approximately three to four months.

Example 3

Twenty volunteers (8 women) participated in this study. The mean age of participants was 54 years old (SD=11 years). Participants had no history of hair implants and had normal eating and sleeping patterns.

Participants first read and signed an informed consent form in which they gained information about the hair regeneration product. They received information that this product JR101s was designed to increase hair growth, that it was based on natural compounds and that use of the product would not lead to harmful effects. Participants received explicit instructions on how to use the product and were asked to apply the product at least once a day on their scalp and not to use any other hair growth or regeneration products for the duration of the study.

In order to measure hair growth, hair thickness and color regeneration participants had a monthly session to screen their progress. In this session photos were taken to measure and count actual hair increase and questionnaires were filled in probing for the effects of the product use.

Questionnaires involved 14 questions and was based on the hair growth questionnaire of Barber (1998). Participants answered by indicating yes or no for each question. The first two questions were: Did you notice new hair growth during the past month?' and 'did you notice new hair growth since the start of treatment?'. The next two questions asked the same question for hair loss: Did you notice any new hair loss during the past month/since the start of the treatment?' The sixth question was: Did you notice more hair loss than before since the start of the treatment?' Next, participants answered the questions: Did you notice that your hairs felt thicker during the past month/since the start of the treatment?' and Did you notice that your hairs felt more healthy during the past month/since the start of the treatment?'. The tenth and eleventh question asked whether hairs felt less fragile during the past month/since the start of the treatment. Finally, questions asked whether they had noticed their hair getting more colour and whether it became less grey/white during the past month/since the start of the treatment.

The questions dealt with a number of issues and were aimed to probe noticeable differences, both during the last month and since the start of treatment. First, results were discussed for hair growth and hair loss. Than findings dealing with healthiness of the hair and strength and thickness were discussed. Finally, evidence for colour change were discussed.

Hair growth was probed with a two different questions. In FIG. 26 data for noticeable hair growth is presented, both for hair growth during the past month and since the start of treatment. After 1 month of treatment 47% of participants noticed new hairs growing. After 6 months of treatment, 94% of participants had noticed new hair growth.

Questions probing for hair loss asked whether participants had noticed that any of the new hairs fell out and whether hair loss had increased since the start of the treatment. Over the whole course of the treatment, 14% of participants had noticed that some new hairs fell out. 20% of participants indicated that at some point during the treatment they noticed an increase in hair loss since the treatment. Additional questions indicated that participants felt that this hair loss was due to more healthy hair taking the place of old, fragile hair.

FIG. 27 shows the answers for the questions probing for new hair loss during the last month and more hair loss since the start of the treatment. Note that the data of the two alopecia patients were not taken up for these questions nor for any of the following questions.

The questions for healthiness of hair, thickness and fragility lead to similar answers for all participants, suggesting that they felt hair to become more healthy, thicker and less fragile.

Approximately 85-92% of participants had noticed an increase in healthy hair, thicker hair and less fragile hair during the treatment (FIG. 28).

The final question asked participants whether they had noticed their hair getting more colour (e.g., less white/grey hair). For analysis of answers to these questions we only included the data of participants who had white/grey hair before the start of the treatment. Results indicate that all participants with white/grey hair noticed a significant increase in colour during the course of treatment (FIG. 29).

For each participant one specific place was chosen for hair growth analysis. Typically, this was a bald spot or a spot with thinning hair. Hair growth was measured by counting and estimating the total amount of thick/thin hairs on the specific spot, on the basis of the digital analysis photograph.

A first analysis was one on the data of bald participants, including alopecia patient data. On average, the data provide clear evidence that both fine hairs and more thick hairs suddenly started to grow for participants who had no hair at the probed place (FIG. 30).

For balding participants, we investigated % increase in total hair. These data clearly show a remarkable increase in hair growth. After 6 months, there was a 3 tot 4 times overall increase in both long fine and thick hairs (FIG. 31).

Analyses of data about thin and thick hair clearly show that participants with thin hair get a significant increase in the amount of thick hair (FIG. 32).

Following the results of the questionnaires, data from participants with white/grey hair clearly show evidence that participants' hair gets more colour (FIG. 33).

The data obtained via questionnaires and photo analyses provide clear evidence that the composition containing the compound of formula (I) of the present invention is highly effective in regenerating hair growth. Data suggest that application of the composition containing the compound of formula (I) of the present invention to the scalp leads to a significant increase in total amount of hairs, even in participants who had no hair at the probed place and in participants who have a clinical condition of alopecia totalis. Moreover, results suggest that the formula is potent at reviving the hair, leading to thicker and more healthy hairs as well as hairs with original hair colour. Overall these results suggest a regeneration of the hair and cells involved in the hair growth cycle.

However, it is clear that there is some individual variance in treatment effects. That is, not all participants showed the same increase in hair growth and healthy hair. Though this could be the result of a number of different factors, stressful factors and nutritional factors are likely involved.

In conclusion, the aim of this study was to examine whether the application of a lotion based on formula HRF1 would change hair growth significantly. The results obtained over a time period of more than six months were analysed. The results suggest that the composition containing the compound of formula (I) of the present invention is highly effective at increasing hair growth.

Example 4

One woman with brittle nails and a long lasting nail fungus problem, treated the nails of her foot twice daily for a period of one month. The nails became stronger and more shiny and the fungus in her toe gradually disappeared. After one month the toe was completely fungus free.

Experimental Data

Cream Preparation (Cosmetic and Therapeutic):

The cream with JR101s as active ingredient/product for a pilot production was made according to following protocol: oil preparation:

Example of dilution 1/100: 40 mL (JR101s impure)+ and 4 liters of oil (e.g.: jojoba or olive oil)=product A One method of preparation is to agitate or vigorously mix both JR101s with the base oil to achieve oil product A which forms the basis of any type of topical application.

Another alternative method of preparation is to macerate the compound JR101s with the base oil. Maceration is a well know process. The preferred method of maceration is to add the compound JR101s with the base oil at the above mentioned ratio and agitate 5 minutes a day for 2-3 weeks at room temperature. The JR101s compound will optimally be mixed with the base oil and purified.

After the maceration process the man skilled in the art will notice that the product A has two faces (an upper phase: oil phase+a lower phase: aqueous phase). The man skilled in the art will then take the oil face being the purified part of the maceration process. Maceration delivers a somewhat more purified product but is not essential to the efficacy of the finished product as no toxic elements will enter the skin.

The following protocol illustrates some of the possible mixtures of a JR101s based cream, ranging from a very oily based cream for skin applications to a more aqueous base spray for hair growth applications, with JR101s mixed pure with the base oil or in a macerated form mixed with the base oil.

TABLE 4

| Ingredients of the cream | General range (% wt) | preferred value (% wt) | Pilot production of 100 liters of the cream of the present invention |
|---|---|---|---|
| Water | 0-99.9 | 57 | 57 |
| JR101s (pure or macerated) | 0.1-99.9 | 13 | 13 |
| acceptable vehicle = base oil (e.g. jojoba or olive oil) | 0-99.9 | 7 | 7 |
| Emulsifier (e.g. tefose ® 2000) | 0-50 | 3 | 3 |
| Propylen Glycol | 0-99.9 | 20 | 20 |
| total | | 100 | 100 |

Comparative Study of Collagen Recovery Between (the Topical Composition (Cream)+JR101s and the Topical Composition (Cream) without JR101s (Placebo)).

TABLE 5

| Topical composition | % of collagen recovery from 6 to 48 months | % of hair growing from 6 to 48 months | % of skin recovery from 6 to 48 months |
|---|---|---|---|
| Cream (Base oil + JR101s at 13% wt) | (45-100) ± 10 | (65-90) ± 12 | (80-95) ± 12 |
| Cream (Base oil − JR101s) = placebo | (10-12) ± 15 | (7-9) ± 10 | (15-18) ± 19 |

The results of a comparative study of collagen recovery between (topical composition+JR101s and without JR101s (placebo)) is given in table 5, the first value in brackets corresponding to a 6 months treatment and the second to a 48 months treatment), and 100% collagen or skin recovery corresponding to the total collagen in the skin and 100% hair growing to the presence of hairs of 2 to 6 cm long. In table 5 the base oil used is olive oil.

In conclusion, the hair growing effect and the skin recovery are directly involved with collagen recovery. The compound JR101s has positive effect in collagen recovery.

The placebo test (control) of table 5 using base oil only (olive oil or jojoba oil) shows fluctuating collagen levels but no upward trend and confirms the JR101s action in collagen recovery. It is clear that the placebo study shows some collagen recovery but due to the standard variation it also shows that the subjects lost collagen. This is normal as collagen levels go up and down depending on exposure at external factors such as sun (UV), stress and nutrition. The Standard +− deviations should reflect that. Therefore the surprising effect (% of collagen recovery and % of hair growing from 6 to 48 months) is only due to the active compound of formula (I) of the present invention, i.e. JR101s).

A man skilled in the art would know that the results mentioned in table 5 (when using JR101s with a base oil) would not be obtained by a simple massage of the skin head. The results obtained by a simple massage of the skin head would be similar or even lower than those obtained when using the placebo.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES

[1] Ulf Peters: Thesis: Studies Towards Anti-Bredt Ring Systems of Natural Products, the University of Tennessee, Knoxville, August 2002
[2] Gert Köbrich: Bredt Compounds and the Bredt Rule. Angew. Chem. Internat. Edit 1973
[3] A study of the effects of Strain on the Structure and Reactivity of Bridgehead Olefins: Lease, T. G., et al J Am Chem Soc 1993
[4] Wilhelm F. Maer and Paul von Rague Schleyer: Evaluation and Prediction of the stability of Bridgehead Olefins. J. Am Chem Soc 1981, 103, 1891-1900
[5] Stephen L. Mayo et al: DREIDING: A Generic Force Field for Molecular Simulation. J. Phys Chem. 1990, 94, 8897-8909.
[6] Bartlett S, Bolt A, Ironmonger A, Joce C, Nelson A, Woodhall T. Configurational stability of bisindolylmaleimide cyclophanes: from conformers to the first configurationally stable, atropisomeric bisindolylmaleimides. Chemistry. 2005 Oct. 21; 11(21):6277-85.
[7] Li C1, Choi P. Molecular dynamics study of the molecular weight dependence of surface tensions of normal alkanes and methyl methacrylate oligomers. J Phys Chem B. 2006 Apr. 6; 110(13):6864-70. Curcio, N. M. & Parish, L. C. (2009). Injectable fillers: An American perspective. *Giornale Italiano di dermatologia venereologia*, 3, 271-279.
DermaLab Combo (2010). *Cortex* Technology, Denmark.
De Rigal, J., Escoffier, C., Querleux, B., Faivre, B, Agache, P, & Lévêque, J. J. (1989). Assessment of aging of the human skin by In vivo ultrasonic imaging. *J Invest Dermatol.* 93, 621-625.

The invention claimed is:

1. A compound having a structure according to Formula (I):

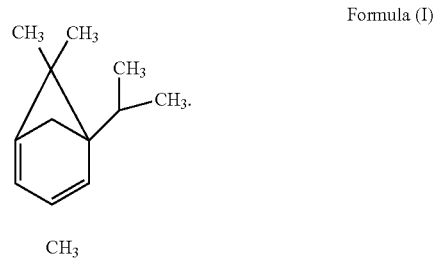

Formula (I)

2. A topical composition comprising the compound of claim 1 in combination with a pharmaceutically acceptable vehicle.

3. The topical composition of claim 2, wherein the compound of claim 1 is present in an amount effective to at least one of prevent heat burns in human skin, prevent chemical burns in human skin, prevent alopecia in human skin, prevent baldness, treat heat burns in human skin, treat chemical burns in human skin, treat baldness, and treat alopecia in human skin.

4. The topical composition of claim 2, wherein the pharmaceutically acceptable vehicle comprises olive oil or jojoba oil.

5. The topical composition of claim 2, wherein the topical composition is formulated as a cream.

6. The topical composition of claim 2, wherein the topical composition comprises 0.1% to 15% by weight of the compound of claim 1.

7. The topical composition of claim 2, further comprising at least one of palmitic acid, palmitoleic acid, erucic acid, eicosenoic acid, docosenoic acid, oleic acid, and linoleic acid.

8. The topical composition of claim 2, wherein the compound of claim 1 is present in an amount effective to stimulate at least one of DNA repair, cellular repair, wrinkle reduction, redness reduction, pigment reduction, UV damage reduction, anti-oxidant effects, barrier repair, increased emollient characteristics, increased moisturizer characteristics, increased collagen production, reduction in the appearance of abnormal skin lesions, reduction in nail fungal damage, and reduction in UV damage.

9. A method of improving a cosmetic parameter in a human comprising administering the topical composition of claim 2 to a human in need thereof in an amount effective to improve the cosmetic parameter, and wherein the cosmetic parameter is selected from the group consisting of alopecia, baldness, collagen and elastin in human skin, growth of hair or nail, rejuvenation and repair or skin, and rejuvenation and repair of nails.

\* \* \* \* \*